US007237205B2

(12) United States Patent
Sarel

(10) Patent No.: US 7,237,205 B2
(45) Date of Patent: Jun. 26, 2007

(54) PARAMETER EVALUATION SYSTEM

(75) Inventor: Oded Sarel, Even Yehuda (IL)

(73) Assignee: Home-Medicine (USA), Inc., Even-Yehuda (IL)

(*) Notice: Subject to any disclaimer, the term of this patent is extended or adjusted under 35 U.S.C. 154(b) by 0 days.

(21) Appl. No.: 10/608,336

(22) Filed: Jun. 30, 2003

(65) Prior Publication Data

US 2004/0008219 A1    Jan. 15, 2004

Related U.S. Application Data

(62) Division of application No. 09/614,546, filed on Jul. 12, 2000, now abandoned.

(51) Int. Cl.
 *G06F 3/00* (2006.01)
 *A61M 16/00* (2006.01)

(52) U.S. Cl. ............... 715/786; 715/787; 128/204.21; 128/204.18

(58) Field of Classification Search ........ 345/706–712, 345/727–728, 765–769, 772–773, 788–789, 345/771, 802, 805, 800, 831–833, 853; 128/204.18, 128/204.21, 903, 897; 715/784, 785, 786, 715/787
See application file for complete search history.

(56) References Cited

U.S. PATENT DOCUMENTS

| 3,688,413 | A | 9/1972 | Harte ............... 35/9 E |
| 3,786,510 | A | 1/1974 | Hodges ............. 346/33 ME |
| RE28,513 | E | 8/1975 | Suzuki et al. |
| 4,216,462 | A | 8/1980 | McGrath et al. ...... 340/150 |
| 4,351,344 | A | 9/1982 | Stenzler |

(Continued)

FOREIGN PATENT DOCUMENTS

| EP | 0251520 | 7/1988 |
| IL | 105547 | 4/1993 |
| WO | WO 98/02083 | 1/1998 |
| WO | WO 01/30231 | 3/2001 |

OTHER PUBLICATIONS

Microsoft Screen Captures, Microsoft Windows Version 4.0, Copyright 1981-1998, Figures 1-11.*
"The health.net Industry—The Convergence of Healthcare and the Internet", Jun. 8, 1999, pp. 1-38 , Fitzgibbons, Stephen et al. http://www.schiller.ch/about.htm (Web page).

(Continued)

*Primary Examiner*—Ba Huynh
*Assistant Examiner*—Truc T. Chuong

(57) ABSTRACT

A parameter evaluation system comprising a boundary input device for setting boundaries in a variation range of one or more parameters, thereby to define regions within said variation range, a label input device for associating labels with said regions, a rule input device for setting rules to associate at least one of a plurality of output recommendations with each of said regions and with combinations thereof and an output device to present a user with an output recommendation associated with a region or combination thereof corresponding to at least one measured parameter input to said system. The input device is a parameter value region selection and categorization input device for setting boundaries in the variation range of the parameter, defining regions therebetween and categorizing the regions. The device comprises a visual representation of the variation range as a linear continuum, a continuum divider for visually dividing the continuum at user selectable points therealong, the points corresponding to values of the parameter, thereby to define regions therebetween and a category definer for defining categories for association with the regions. The device has an application in a patient monitoring kit under remote supervision of a physician.

22 Claims, 38 Drawing Sheets

Systolic blood pressure

U.S. PATENT DOCUMENTS

| | | | |
|---|---|---|---|
| 4,367,752 A | 1/1983 | Jimenez et al. ............. 128/689 |
| 4,489,610 A | 12/1984 | Slavin ......................... 73/585 |
| 4,561,449 A | 12/1985 | Hu et al. .................... 128/746 |
| 4,671,772 A | 6/1987 | Slade et al. ................. 434/219 |
| 4,740,072 A | 4/1988 | Griffin et al. ............... 351/243 |
| 5,002,055 A | 3/1991 | Merki et al. |
| 5,002,491 A | 3/1991 | Abrahamson et al. ...... 434/322 |
| 5,008,853 A | 4/1991 | Bly et al. .................... 364/900 |
| 5,019,974 A | 5/1991 | Beckers ................. 364/413.02 |
| 5,088,981 A | 2/1992 | Howson et al. |
| 5,165,417 A | 11/1992 | Murphy, Jr. |
| 5,197,332 A | 3/1993 | Shennib ........................ 73/585 |
| 5,262,944 A | 11/1993 | Weisner et al. |
| 5,298,021 A | 3/1994 | Sherer |
| 5,306,154 A | 4/1994 | Ujita et al. .................. 434/218 |
| 5,310,349 A | 5/1994 | Daniels et al. .............. 434/350 |
| 5,375,199 A | 12/1994 | Harrow et al. |
| 5,422,690 A | 6/1995 | Rothberg et al. ........... 351/209 |
| 5,451,162 A | 9/1995 | Parsons ........................ 434/16 |
| 5,473,537 A | 12/1995 | Glazer et al. ............. 364/419.2 |
| 5,517,405 A | 5/1996 | McAndrew et al. ........ 364/401 |
| 5,520,192 A | 5/1996 | Kitney et al. |
| 5,542,420 A | 8/1996 | Goldman et al. ........... 128/630 |
| 5,549,117 A | 8/1996 | Tacklind et al. ............ 128/716 |
| 5,553,609 A | 9/1996 | Chen et al. .................. 128/630 |
| 5,619,991 A | 4/1997 | Sloane ......................... 128/630 |
| 5,623,598 A | 4/1997 | Voigt et al. |
| 5,647,834 A | 7/1997 | Ron ............................. 600/23 |
| 5,677,979 A | 10/1997 | Squicciarini et al. ......... 386/46 |
| 5,680,560 A | 10/1997 | Gaertner |
| 5,715,823 A | 2/1998 | Wood et al. ........... 128/660.01 |
| 5,758,652 A | 6/1998 | Nikolic ....................... 128/673 |
| 5,765,563 A | 6/1998 | Vander Schaaf |
| 5,769,074 A | 6/1998 | Barnhill et al. ............. 128/630 |
| 5,791,342 A | 8/1998 | Woodard ..................... 128/630 |
| 5,791,908 A | 8/1998 | Gillio .......................... 434/262 |
| 5,810,747 A | 9/1998 | Brudny et al. .............. 600/595 |
| 5,811,681 A | 9/1998 | Braun et al. .................. 73/585 |
| 5,827,180 A | 10/1998 | Goodman ................... 600/300 |
| 5,840,018 A | 11/1998 | Michaeli ..................... 600/300 |
| 5,842,975 A | 12/1998 | Illyes et al. |
| 5,842,977 A | 12/1998 | Lesho et al. ................ 600/300 |
| 5,848,975 A | 12/1998 | Phillips ....................... 600/532 |
| 5,851,186 A | 12/1998 | Wood et al. ................ 600/437 |
| 5,855,550 A | 1/1999 | Lai et al. ..................... 600/300 |
| 5,859,972 A | 1/1999 | Subramaniam et al. .. 395/200.3 |
| 5,865,733 A | 2/1999 | Malinouskas et al. ...... 600/300 |
| 5,868,134 A | 2/1999 | Sugiyama et al. .......... 128/630 |
| 5,868,135 A | 2/1999 | Kaufman et al. ........... 128/630 |
| 5,873,369 A | 2/1999 | Laniado et al. ............. 128/903 |
| 5,879,292 A | 3/1999 | Sternberg et al. ........... 600/300 |
| 5,892,570 A | 4/1999 | Stevens ....................... 351/237 |
| 5,895,345 A | 4/1999 | Knelson |
| 5,902,234 A | 5/1999 | Webb .......................... 600/300 |
| 5,906,208 A | 5/1999 | Ishikawa et al. ............ 128/898 |
| 5,907,291 A | 5/1999 | Chen et al. ............. 340/870.16 |
| 5,928,160 A | 7/1999 | Clark et al. |
| 5,931,160 A * | 8/1999 | Gilmore et al. ........ 128/204.21 |
| 5,961,446 A | 10/1999 | Beller et al. |
| 5,961,447 A | 10/1999 | Raviv et al. |
| 5,978,292 A | 11/1999 | Lim ............................ 365/201 |
| 6,022,315 A | 2/2000 | Iliff |
| 6,073,046 A | 6/2000 | Patel et al. |
| 6,080,106 A | 6/2000 | Lloyd et al. |
| 6,113,540 A | 9/2000 | Iliff |
| 6,135,951 A | 10/2000 | Richardson et al. |
| 6,168,563 B1 | 1/2001 | Brown |
| 6,168,568 B1 | 1/2001 | Gavriely |
| 6,206,829 B1 | 3/2001 | Iliff |
| 6,222,544 B1 * | 4/2001 | Tarr et al. .................... 345/839 |
| 6,241,683 B1 | 6/2001 | Macklem et al. |
| 6,289,244 B1 * | 9/2001 | Conley et al. ................ 607/27 |
| 6,295,506 B1 | 9/2001 | Heinonen et al. |
| 6,302,844 B1 | 10/2001 | Walker et al. |
| 6,308,102 B1 * | 10/2001 | Sieracki et al. ............... 607/59 |
| 6,320,585 B1 | 11/2001 | Engel et al. |
| 6,322,502 B1 | 11/2001 | Schoenberg et al. |
| 6,364,834 B1 | 4/2002 | Reuss et al. |
| 6,369,838 B1 * | 4/2002 | Wallace et al. ............. 345/810 |
| 6,406,426 B1 * | 6/2002 | Reuss et al. ................. 128/903 |
| 2001/0034717 A1 * | 10/2001 | Whitworth ................... 705/64 |
| 2003/0062045 A1 * | 4/2003 | Woodring et al. ..... 128/204.18 |

OTHER PUBLICATIONS

BACS Profile: Revolutionizing Medical Data Collection & Management, pp. 1-2.

BACS Automated Self Operated Audiometer, Model 101 (Product Description), pp. 1-2.

Panasonic Vital Signs Box (Product Description), Matsushita Electric Industrial Co., Ltd. p. 1, Dec. 6, 1999.

BACS AVAT Model 201: Automated Self-Operated Vision Tester, pp. 1-2.

* cited by examiner

Diastolic blood pressure

Recommendation

- Contact your physician.

- Take another _____ Tablet.
  Repeat B.P. test in two hours.

- Thank you. Repeat test tomorrow.

- Stop for today _____. Drink water
  and repeat B.P. test in two hours.

- Contact your physician. Call an
  ambulance.

Maximum change per test

20%

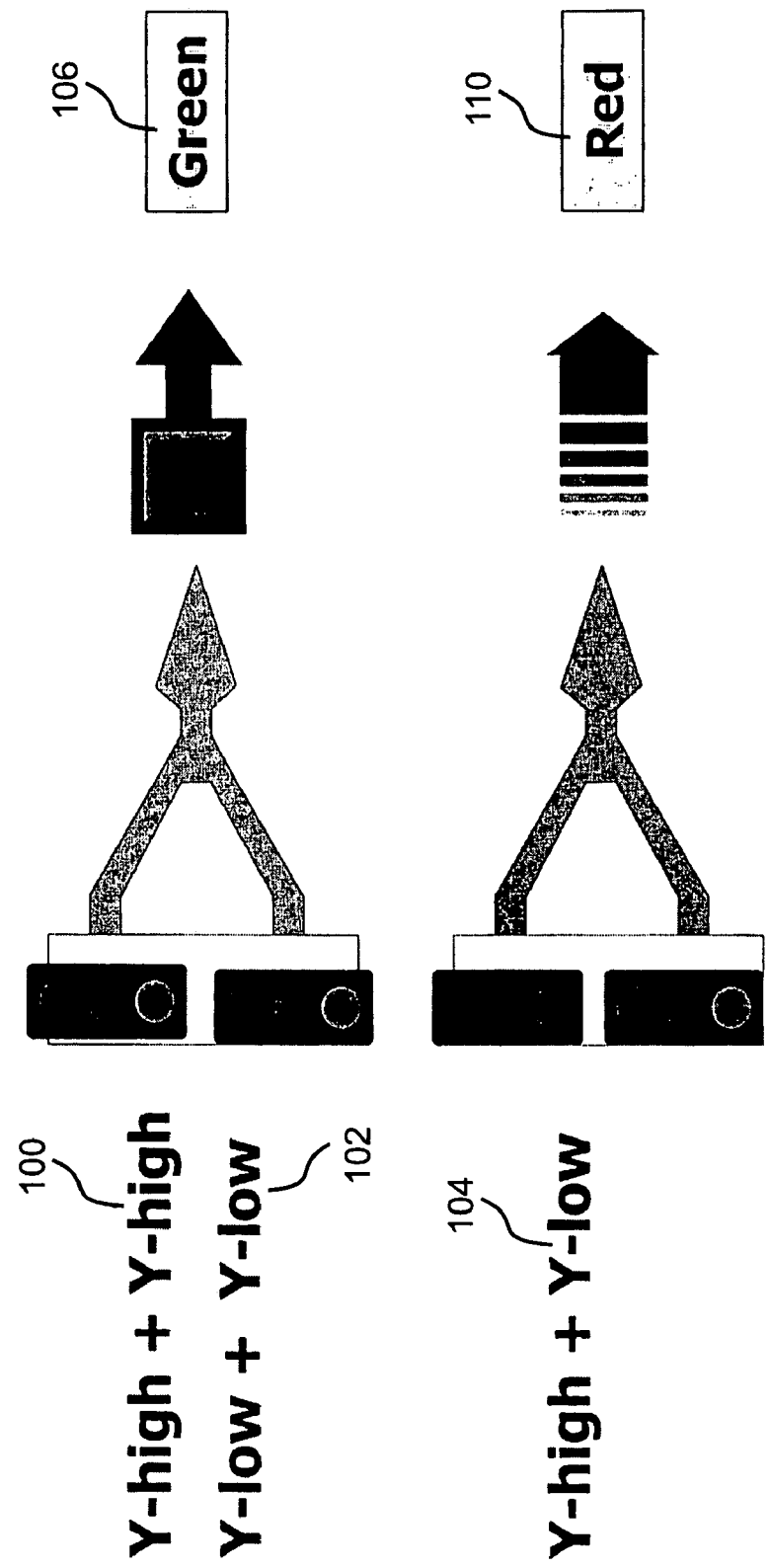

Fig. 15

Patient's notification

Patient receives reaction classified into three categories:

Red:
- Contact your physician A.S.A.P.
- Go to emergency room.

Yellow:
- Specific action item, according to the specific patient and medical condition.

Green:
- No change. Repeat test according to normal scheduling.

Two yellows –
Twenty four different possibilities. Six pairs of high yellow, six of low yellows, and twelve of combined pairs.

Polarity –
In some parameters HMC defines inverse polarity, according to common medical reaction in those parameters.

E.G. –
Urea level is signed (-).

PARAMETER EVALUATION SYSTEM

RELATIONSHIP TO EXISTING APPLICATIONS

The present application is a divisional application of U.S. patent application Ser. No. 09/614,546 filed Jul. 12, 2000, now abandoned.

FIELD OF THE INVENTION

The present invention relates to a parameter evaluation system and more particularly but not exclusively to a parameter evaluation system for use in the medical field.

BACKGROUND OF THE INVENTION

Presently, in the medical field, there, are a number of expert systems that use preset rules to make medical diagnoses and like decisions. Generally, their use has not been accepted by physicians because they are not trusted to make reliable decisions. The physician or other care provider is generally uncomfortable with being unable to see all stages of the decision-making process.

Nevertheless, some form of automation that allows a patient requiring continuing supervision a degree of independence is desirable. For example, a patient may require monitoring of his blood pressure and other parameters whilst undergoing a course of treatment. Certain fluctuations and trends in his blood pressure level may be of considerable interest to his physician but it is not desirable that the patient should contact the physician or other care provider on a highly frequent basis and it is not always practical to provide the patient with a full set of rules for events that should be reported, especially when multiple parameters are involved. It is likewise not always practical to ask a patient to keep records of the monitoring results that could reveal important trends.

A pending patent application, Ser. No. 09/428,430 of the present applicant, which is hereby incorporated by reference, discloses a medical condition sensing system including a multiplicity of general purpose computers disposed in user locations. The computers are connected via a computer network to a controller computer remote from the user locations. Personal parameter measuring software is resident at the user location and the controller computer for measuring a personal parameter of a user, such as heart rate, blood pressure etc. Parameter reference levels are set and the controller computer compares a currently measured personal parameter with a corresponding reference and provides a comparison output. In essence the system awards points for levels of an individual personal parameter measured and decides to take action after a given number of points have been exceeded, the given number being set per user to take into account the parameters being measured and the condition being considered.

The above-described system provides the physician or other care provider with a system that allows a patient to carry out self-monitoring at home, and at the same time ensures that the physician or other care provider will be informed promptly if a certain points threshold is reached.

The above-described system, however, makes decisions on a summation basis, and therefore physicians are not fully confident of being able to receive reliable results in all circumstances.

SUMMARY OF THE INVENTION

Embodiments of the present invention overcome the drawbacks of the prior art by firstly permitting the physician or other care provider to set the scoring rules per each single parameter and the rules for aggregation of parameters independently per patient, and secondly by ensuring that dangerous levels in one parameter cannot be masked by opposite changes in another parameter.

According to a first aspect of the present invention there is thus provided a parameter evaluation system comprising a boundary input device for setting boundaries in a variation range of one or more parameters, thereby to define regions within the variation range, a label input device for associating labels with the regions, a rule input device for setting rules to associate at least one of a plurality of output recommendations with each of the regions and with combinations thereof and an output device to present a user with an output recommendation associated with a region or combination thereof corresponding to at least one measured parameter input to the system.

In an embodiment, the boundary input device comprises a bar having a length representative of a variation range of a respective parameter.

In an embodiment, the boundary input device further comprises slidable boundary points for sliding along the length and wherein the regions are defined between the slidable boundary points.

In an embodiment, the label input device is operable to associate one of a plurality of labeling colors with at least one of the regions.

In an embodiment, the label input device is operable to associate a labeling color with a combination of the regions.

In an embodiment, the label input device is operable to label at least one of the regions with one of a group of categories.

In an embodiment, at least one of the categories is associated with a procedure for making automatic contact with a remote site.

In an embodiment, the procedure utilizes any one of a group comprising internet messaging, telephone messaging, paging and fax messaging to reach the remote site.

An embodiment further comprises an interface for connecting a measuring device thereto.

Preferably, there is further provided a measuring device attached to the interface for providing to the system a measured parameter.

In an embodiment, the parameter is a body medical parameter.

Preferably, there is further provided a list of at least one symptom, selectable by a user and classifiable by the user according to degree of severity, and wherein the rule input device is usable to set rules which incorporate the rule input device with the parameters to produce the output.

In an embodiment, at least one parameter is signable to influence an output.

Preferably the boundary input device comprises a parameter value region selection and categorization input device for setting boundaries in a variation range of a substantially continuously variable parameter, defining regions therebetween and categorizing the regions, the device comprising:

a visual representation of the variation range as a linear continuum, a continuum divider for visually dividing the continuum at user selectable points therealong, the points corresponding to values of the parameter, thereby to define regions therebetween and a category selector for associating one of a group of predefined categories with at least one thus-defined region.

In an embodiment, the continuum divider comprises a user-selectable number of sliders operable to be moved by a user to the user-selectable points.

In an embodiment, each one of the predefined categories has a color associated therewith and wherein the device is operable to display each-thus defined region on the continuum using the color.

Preferably, there is also provided an overlay unit for displaying the continuum in association with data connected with the parameter, thereby to assist in selection of the points.

Preferably, the overlay unit is a graphical overlay unit operable to display the continuum in association with data connected with the parameter and graphically arranged and scaled according to the continuum.

According to a second aspect of the present invention, there is provided a method of associating a series of outputs with detected levels of a plurality of continuously varying parameters, the detected levels comprising an outcome, the method comprising setting one or more boundary levels for each parameter, thereby defining regions between each boundary level, associating categorization labels with each the defined region, associating rules with each region and with combinations of regions of different parameters to associate a series of outputs with the regions and combinations, such that at least one of the series of outputs is produced by an outcome.

In an embodiment, at least one of the parameters is a body measurement and the output is a medical instruction.

Throughout this specification, reference to a physician includes any care provider or health care professional who is responsible for the patient.

BRIEF DESCRIPTION OF THE DRAWINGS

For a better understanding of the invention and to show how the same may be carried into effect, reference will now be made, purely by way of example, to the accompanying drawings, in which:

FIGS. 8a to 8c are generalized diagrams showing a home observation system of a preferred embodiment of the present invention set to produce a different output from that of FIG. 7 from the same combined systolic and diastolic blood pressure measurements.

FIG. 15 is a generalized schematic diagram showing, in greater detail, how a home monitoring system of the present invention is operable to alert a physician to the status of a patient undergoing monitoring.

DESCRIPTION OF THE PREFERRED EMBODIMENTS

Figure 1A:
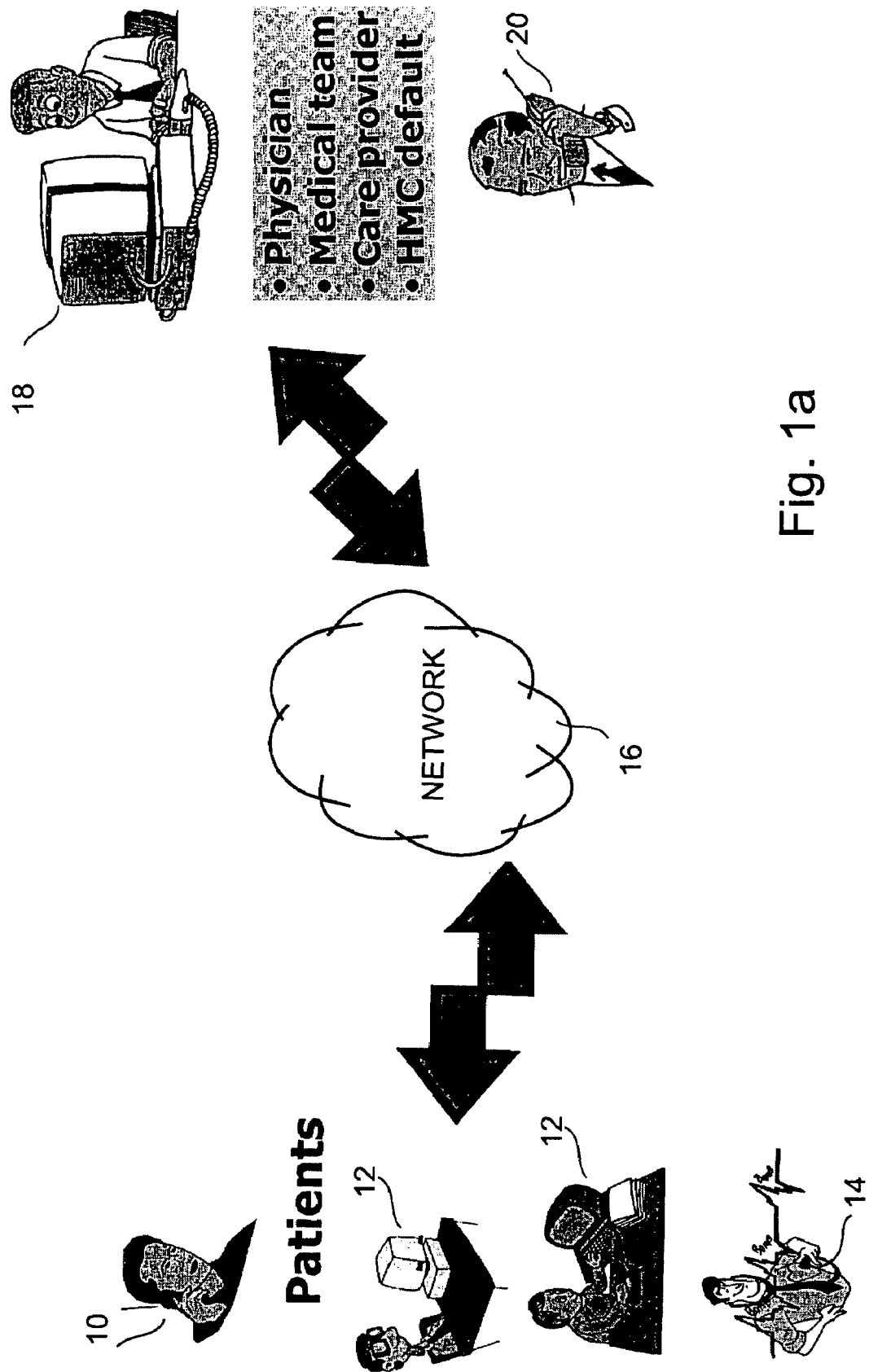
FIG. 1a is a generalized diagram showing a home observation system according to a first embodiment of the present invention.

Reference is now made to FIG. 1a, which is a generalized diagram of a system that supports through one or more central or distributed servers, a variety of data capturing, data exchange, data evaluation and data scoring activities between patients and their care providers. The patient may utilize a variety of devices to enter information and access the system, inclusive of: personal computer, computer, phone, cellular phone, PDA (Personal Digital Assistant), email, pager, medical sensors and others, in order to send information to the system and receive information from the system. The care provider may likewise use a variety of devices to configure and access the system, inclusive of: personal computer, computer, phone, cellular phone, PDA (Personal Digital Assistant), email, pager, medical sensors and others, in order to send information to the system and receive information from the system. The central server(s) enable secure capturing and processing of a variety of patient information, its processing and its distribution to the patients and care providers according to pre-defined rules configurable by a variety of potential authorized users.

In a first embodiment, the patient may be in possession of a data processing device capable of handling low complexity software. Such devices may include a data-enabled mobile telephone 10 or a desktop computer 12. The data processing device is preferably combined with a measuring device 14 able to measure at least one type of body parameter such as pulse rate, blood pressure etc.

The data processing device 10, 12, is preferably able to process data input from the measuring device 14, in a manner that will be described below, in order to give the patient an outcome such as a recommendation for action. Examples of the outcome may be instructions to the patient such as repeat the measurement at a certain time, or that the dosage of a treatment should be stepped up or down, or that the doctor should be contacted immediately or, any other outcome. As will be described below, the outcome is preferably defined by the physician or other care provider.

In an embodiment, the processing is carried out locally with the patient. In another embodiment no processing is carried out with the patient. Instead the measurement results are transferred using voice or tone over the telephone to a server 18 which takes in the information and processes it. It then issues a voice result to the patient. In addition it may automatically alert the physician or other care provider or hospital or order an ambulance.

As another alternative, the data from the measurement apparatus may be added to a form at the local computer 12 such as an HTML or XML form and the form may be processed either locally or remotely depending on the way the system is set up. Measurement data may be inserted into the form either manually using a keyboard or by a touch screen or by voice and voice processing or automatically by connecting the measuring device 14 to the computer 12, for example via the serial port. Again, such a system may automatically alert the physician or hospital or order an ambulance.

The system advantageously makes use of unified messaging so that the patient can send information via any messaging media. It may be more convenient in any given circumstances, to use the standard telephone network or fax or the Internet or any other type of available connection. A particular physician may set up the system so that patients having Internet are set up to use the Internet as the means of contacting a central server. Those that do not have an Internet connection use the telephone where a voice recognition system based on the server is able to take voice instructions and answer using voice, or where the telephone keypad is used for data entry.

Likewise from the physician's point of view, he may wish to be notified immediately of urgent patient conditions and thus would like calls to be put through to a pager or to his mobile telephone if he cannot be contacted at his surgery, office or home. When he can be contacted at his surgery, office or home he may prefer to be contacted via the Internet for most situations. For extremely urgent situations the system may contact a hospital and/or order an ambulance.

The use of unified messaging with a voice recognition facility allows for such flexible use of the communications network. A suitable voice recognition system is commercially available from Nuance Inc. of California USA.

The use of unified messaging permits the physician to program the system with a hierarchy of ways of contacting him. At the top of the hierarchy may be e-mail to his desk. At a lower end of the hierarchy there may be a mobile telephone and/or a pager and finally there may be a facility for leaving a notification at his desk if all other methods fail to reach him.

Figure 1B:
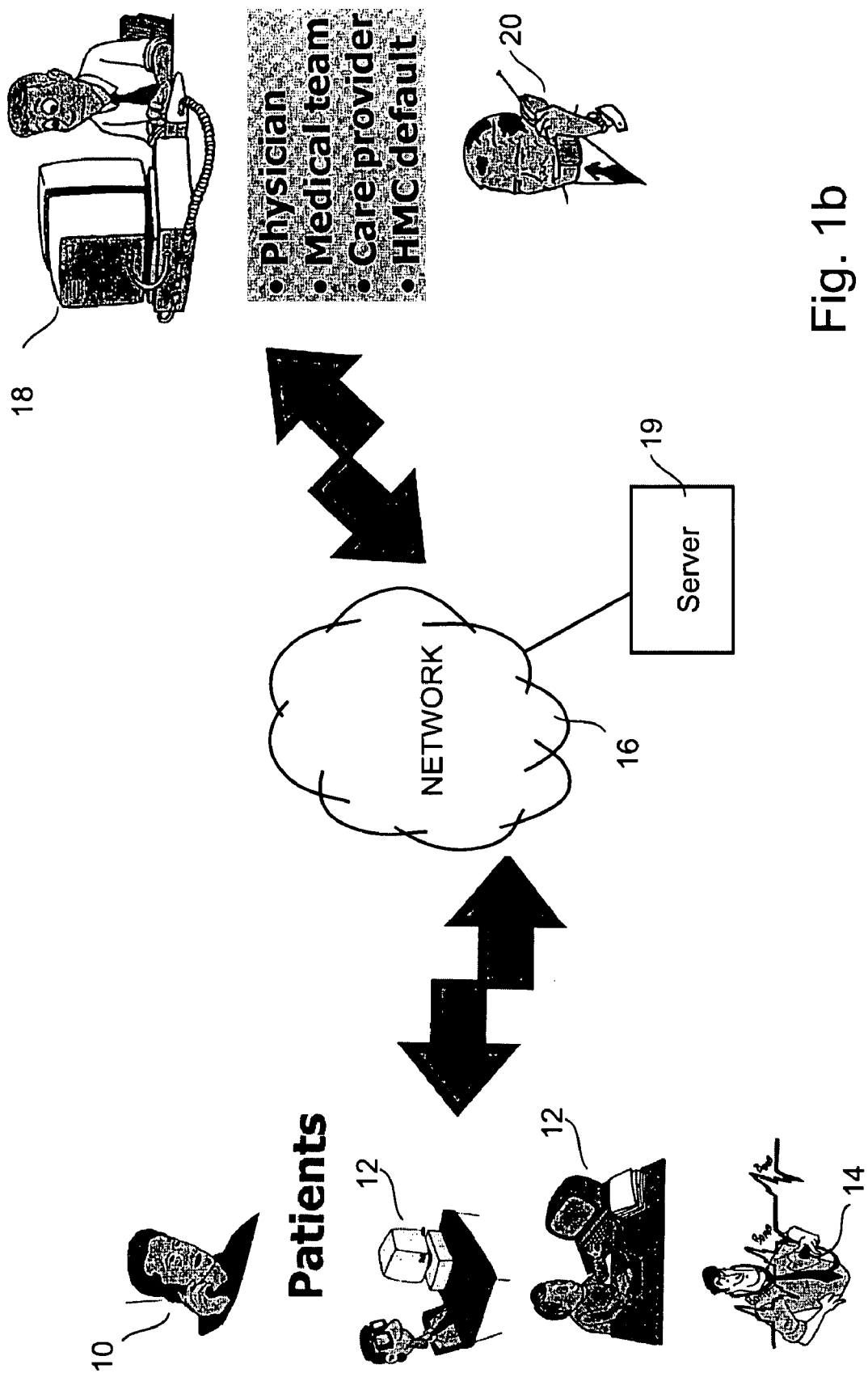
FIG. 1b is a generalized diagram showing a variation of the device of FIG. 1a, FIG. 2 is a generalized block diagram of the system according to FIG. 1a, FIG. 3 is a generalized diagram illustrating an operating principle of the present invention.

Reference is now made to FIG. 1*b* which shows a second embodiment of the present invention. In the embodiment of FIG. 1*b* Parts that are identical to those shown above are given the same reference numerals and are not referred to again except as necessary for an understanding of the present embodiment. FIG. 1*b* differs from FIG. 1*a* in that a server 19, preferably associated with the network 16, supports one or more users of the home monitoring system, who are able to communicate with it using any form of unified messaging, that is to say vocally, digitally via the typed word, digitally via data files, or in any other way. The server is able to process the data received, in the manner that will be described below, send responses to the user and pass it on to a physician or other care provider or to a staffed center.

Figure 2:
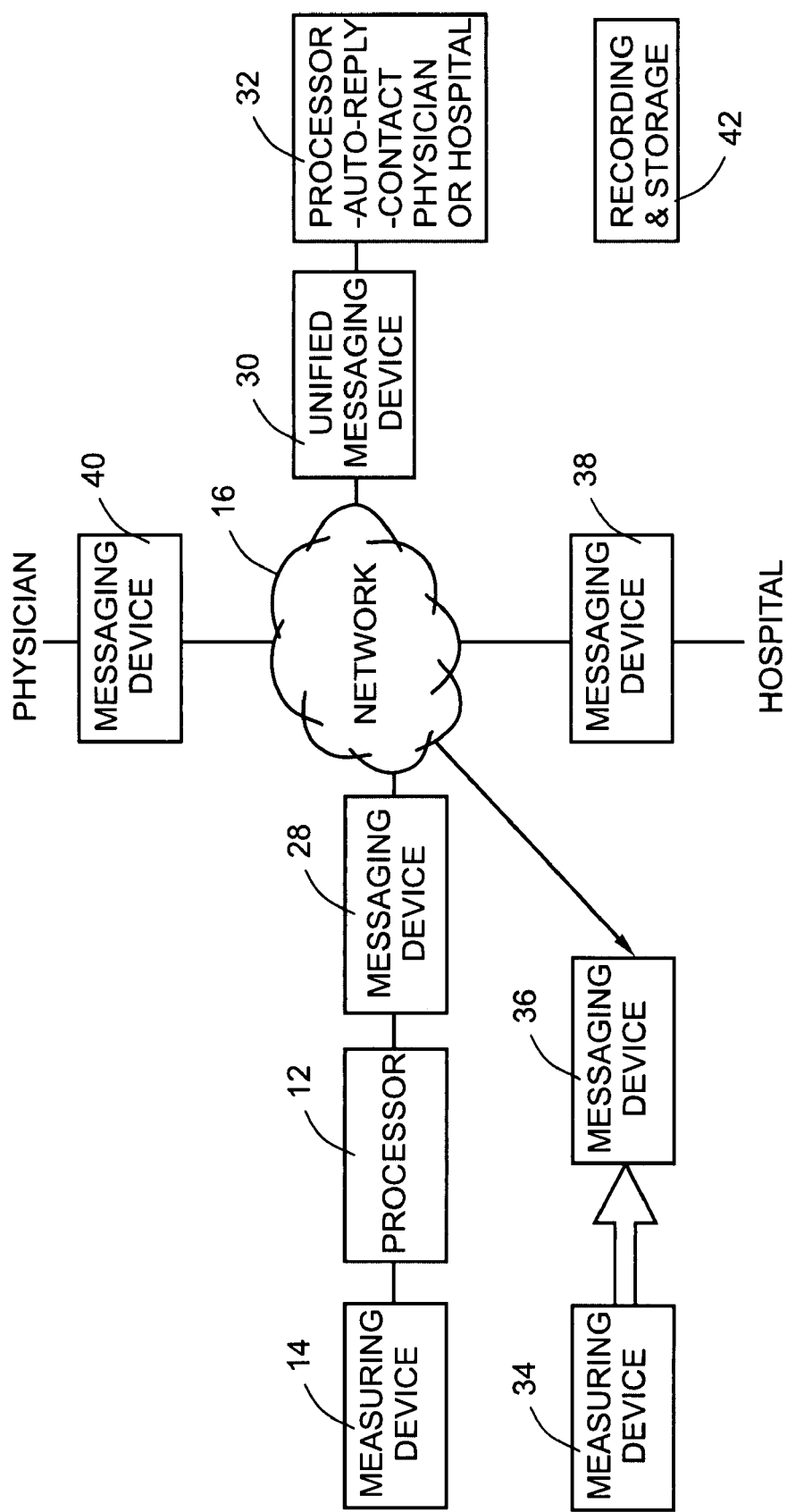

Reference is now made to FIG. 2 which is a generalized block diagram showing in greater detail the system that has been described above in respect of FIG. 1. In FIG. 2, parts which are the same as those described in the previous figure are given the same reference numeral and are not described again except as necessary for an understanding of the present figure. The measuring device 14 is preferably connected to a data processing device 12. In accordance with a preferred embodiment of the invention, personal parameter measuring software 20 is resident on at least one of the data processing devices 12 and/or on at least one server 32 for measuring at least one personal parameter of at least one patient, being a user of one of the general purpose computers. The personal parameters may be any suitable medical parameter, such as, for example, parameters relating to heart function, lung function, hearing, vision, alertness, physical appearance and perception as well as conventional medical indications such as weight, height, age, blood pressure, blood sugar level and other body fluid parameters, as well as various combinations of the foregoing.

Personal parameter measuring software preferably cooperates with measuring device 34 which is preferably adapted to measure each type of personal parameter in association with a general purpose computer 10. Various types of measuring devices 34 may be provided to users of the system. For example, a stethoscope transducer and lung sounds interface may be provided for sensing lung sounds, electrocardiogram electrodes and an electrocardiogram interface may be provided for electrocardiogram measurements, and a hearing testing headset and headset calibrator may be provided for hearing testing.

It is appreciated that various calibration functionalities, which may be embodied in hardware, software or combinations thereof, may be provided as part of measuring device 14 or for use therewith. The calibration functionalities may or may not involve communication with the server 32 via the network 16. A given calibration functionality may operate automatically without operator intervention. Alternatively, a calibration functionality may require operator activity.

It is further appreciated that at every appropriate stage of operation, suitable instruction may be provided to the user by the data processor 12 of the user. This instruction may be presented to the user in textual, audio or multi-media form and may be unidirectional or interactive. Preferably, suitable instruction is provided prior to calibration of measuring device 14, prior to establishment of a baseline and prior to each test.

The data processor 12 is in turn connected to a messaging device 28 which may be a modem or a fax or a telephone or a cellular phone or any other messaging device. The messaging device 28 is operative to send data through a network to a unified messaging device 30. The network may for example be the Internet or other wide area network or a LAN. In the case of a telephone, fax or cellphone, the network will be the public switched telephone network.

The unified messaging device 30 may be connected to or may be part of a server 32 on which are based data processing routines of the type to be described below for processing measurements made by the messaging device 14. Alternatively some or all of the data processing could be performed at the processor 12. The unified messaging device 30 is operative to receive messages from any messaging device.

As an alternative, the patient may be given a measuring device 34 which has a data readout. The user manually inserts the readout data, perhaps using a keyboard, into his messaging device 36, which may be a computer or a telephone or any other suitable messaging device. In the case of a telephone the data could be spoken into the telephone provided that appropriate voice recognition software is available at the receiving end.

Thus an embodiment of the invention in which the user is required to use a telephone to contact the server 19 may typically utilize voice recognition software at the server 19. The user contacts the server which automatically greets the user and preferably asks for a user name or number. The name or number may be spoken in to the phone or keyed in using the keypad. Then the user may be asked to speak or key in the results of particular tests and finally the user may be given spoken instructions as to how to proceed. The server processes the data received as with other methods of data capture, as will be described below and the physician is contacted as necessary.

In accordance with a preferred embodiment of the present invention the medical condition sensing system of the present invention includes personal parameter reference generating software, preferably usable by the physician as will be described below. The personal parameter reference generating software may typically be resident on a general purpose computer to which the physician has access including the server 32, for establishing a reference for the at least one personal parameter. In this preferred embodiment, personal parameter comparison software, resident on the data processor 12 and/or on at least one server 32, compares at least one currently measured personal parameter with a corresponding reference and provides a comparison output.

A comparison output may be provided to the user by the data processor 12 together with an action recommendation. Alternatively or additionally, it may be provided to a controller computer 16 for comparison with reference data stored on a central database 34 in order to provide additional information and recommendations to the user.

A manned center may be associated with the server 32 for providing a human interface and/or input as required. The manned center, which is preferably staffed by physicians or other health professionals, and in particular by the user's personal physician or health care professional, may be in direct telephone or possibly videophone contact with the user. Thus video cameras (not shown) are preferably provided both at the manned center 36 and at various user locations.

In accordance with a preferred embodiment of the, present invention, acceptable ranges of values for various medical parameters used in the present invention and different response regions within those ranges may be established by medical personnel in the manned center 36 in accordance with the personal characteristics of each given patient, as will be described below. Such settings are preferably carried out by the patient's personal physician.

As necessary, the server 32 is able to contact other messaging devices 38 and 40 which may be for example the physician or the hospital.

In accordance with one preferred embodiment of the present invention, communication with the manned center may be actuated automatically by the system, for example in response to a sensed personal parameter or to the comparison output being beyond a given threshold, for example being a red parameter as will be described below. Communication with the manned center may also be initiated by a user, at the user's initiative. Communication between the user and the manned center may be via the network 16 including via conventional telephone or video-conference facilities.

Further in accordance with a preferred embodiment of the present invention, there is provided a recording and storage facility 42 for off-line communication between the physician/care provider and the user, preferably associated with the server 32, for recording and storing sensed, personal parameters.

There may also be provided for operation in the data processor 12 or in the server 32, software providing a comparison facility for comparing personal parameters and a result categorization facility for category regions to a comparison result in accordance with rules set by the physician on a per patient or per group of patient basis as will be described below and providing an indication of a selected category. The software may include signal processing functionality, where the measurement requires it.

Additionally in accordance with a preferred embodiment of the present invention, there is provided additional software which controls measurement of the personal parameters and which may communicate via the network 16 with at least one remote computer. The measurement control software, which may reside both at data processor 12 and at server 32, preferably provides encryption encoding of information liable to be communicated over insecure parts of network 16.

Preferably, there is associated with each data processor 12, standard interface devices which may include at least one of a display, a printer and an audio input/output transducer, as well as a user graphics interface such as a mouse and an IP telephone. A conventional telephone is preferably available at each user location in addition to the messaging device 28 which may be a modem.

In accordance with a preferred embodiment of the present invention communication between a data processor 12 via the network 16 with another data processor 12 or with a server 32 is encoded or encrypted using conventional technology suitable for this purpose.

In one embodiment, the server 32 is provided with access to medical databases which provide reference material for presentation to the user as well as information which can be used by the server 32 or by the physician to evaluate measured personal parameters and to determine suitable courses of treatment therefore and suitable parameter boundaries and rules, as will be explained below.

In accordance with a preferred embodiment of the present invention, the home observation system of the present invention includes:

a multiplicity of general purpose computers or other data processing devices disposed in user locations and being connected via a network such as a computer network to at least one server remote from at least one of the user locations;

personal parameter measuring software resident on at least one of the multiplicity of general purpose computers and at least one controller computer for measuring at least one personal parameter of at least one user; and personal parameter analysis software resident on at least one of the multiplicity of general purpose computers and the at least one controller computer for analyzing at least one personal parameter of at least one user.

The distributed processing thus provided has a number of advantages, including reduced communication load and increased speed of response. Furthermore, such processing enables medical confidentiality to be readily maintained in communications over the computer network.

Preferably, at least one of the general purpose computers and the at least one controller computer serves as a backup for another one of the general purpose computer and the at least one controller computer.

This backup functionality preferably enables the system to overcome computer failures at either a general purpose computer at a user location or a controller computer, by transferring computing functionality to another computer connected thereto via the computer network. Should a network failure occur, but the general purpose computer at the user location is functioning, the user nevertheless can receive basic information as well as indications and recommendations as described hereinbelow from the general purpose computer. Additionally, as the system uses unified messaging, a bypass telephone connection may be employed to provide necessary communication with a user.

Figure 3:
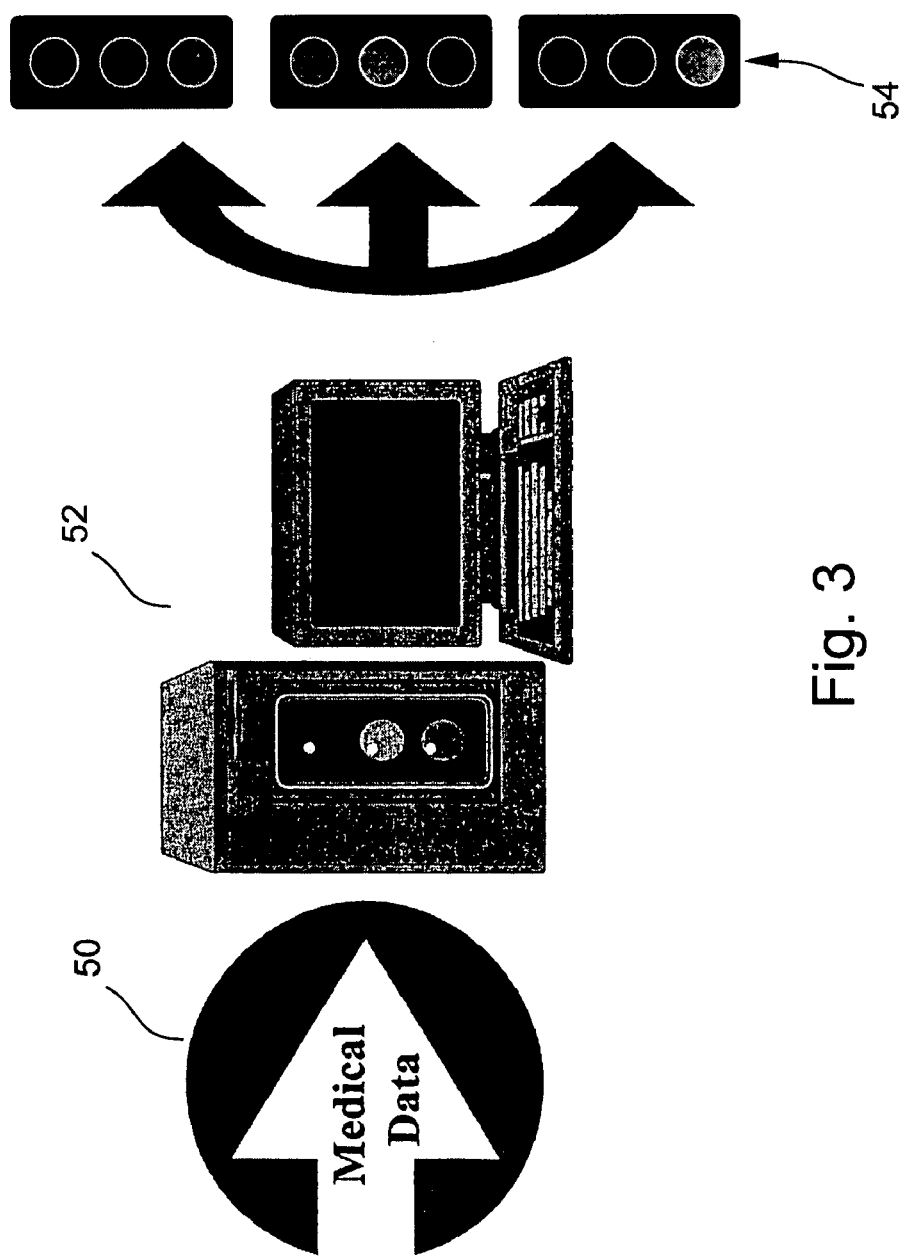

Reference is now made to FIG. 3 which is a schematic diagram showing a general principle behind a preferred embodiment of the present invention. Medical data 50 which has been obtained from measurement device 14 is input into a processor device 52. The processor processes the data only in accordance with a series of boundary levels and combination rules that have been set specifically by the physician for a given patient or group of patients. The input data may contain the results of a plurality of measurements. Each separate result is preferably analyzed into results 54. The results are a series of categories, for example red, amber and green, wherein red is a serious medical condition category indicating that immediate outside professional medical intervention is necessary in its own right, amber is a less serious category indicating, perhaps that action should be taken by the patient but outside professional medical intervention is not necessary unless the result is combined with results of other more serious indications.

It should be noted that more or less than three categories may be used as appropriate and that individual categories may be divided into subcategories. For example the red category may be divided into a low red category indicating making contact with a physician and a high red category indicating that an ambulance should be called urgently.

In general, the patient is given an indication of his current medical condition in the three color categories presentation with the associated recommendations or orders. The physician preferably receives red category results immediately and the remainder as trend or pattern data.

The measurement values are preferably associated with result categories fully in accordance with settings made by the physician for the individual patient or a group of patients as will be explained below.

Although FIG. 3 shows three categories of results, and as mentioned above, sub-categories are also possible and the skilled person will appreciate that new categories could be defined. The creation of new categories could be made as part of the system definition at programming or setup time or it could be offered to the physician to set up new categories on a per patient basis or a per group of patients basis.

Figure 4:
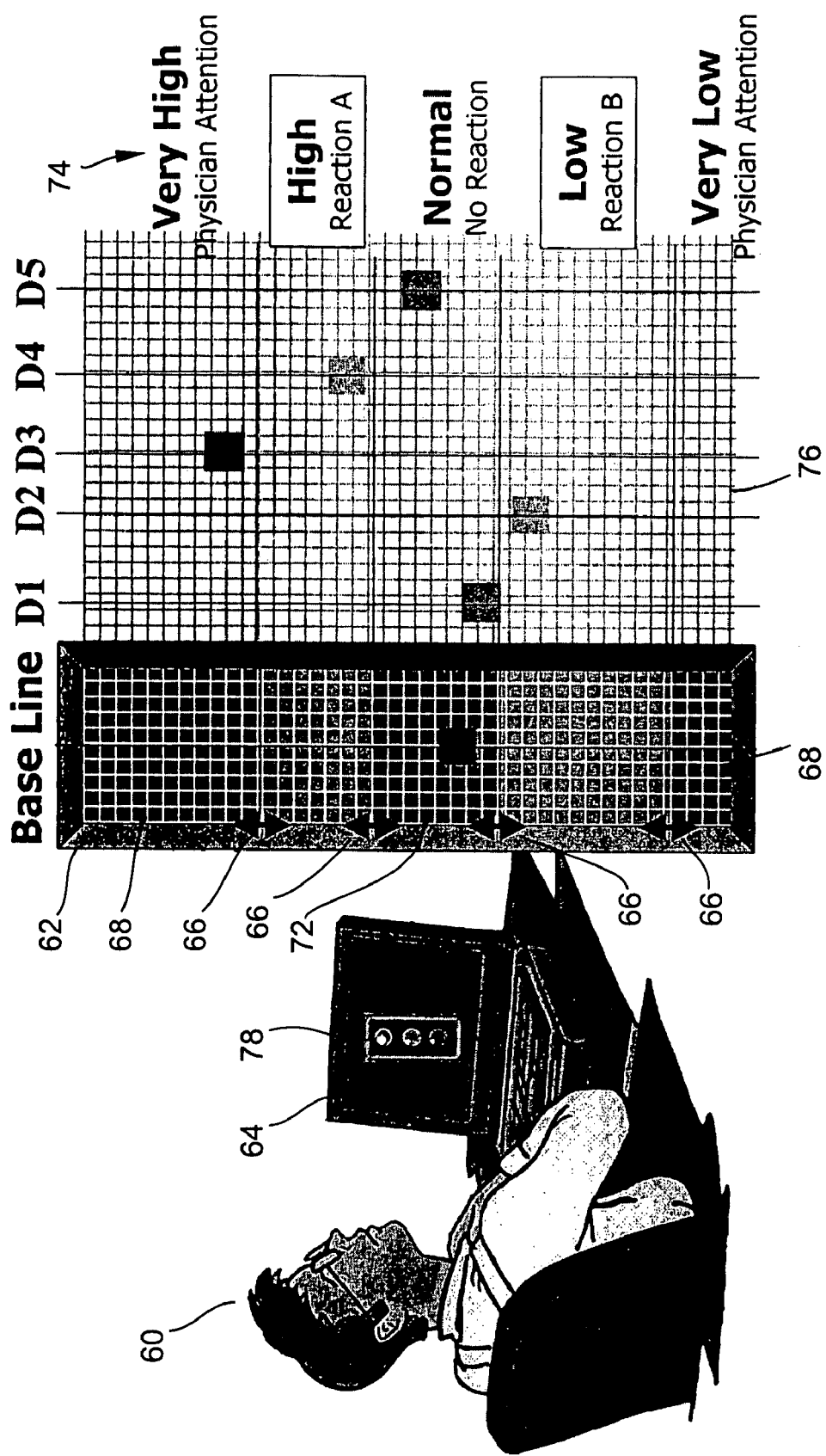
FIG. 4 is a generalized diagram showing a physician setting a home observation system of an embodiment of the present invention for a patient.

Reference is now made to FIG. 4, which indicates a physician 60 setting parameter boundaries for categorizing results of a particular measurement.

In FIG. 4 the physician 60 makes use of a parameter value region selection and categorization tool for setting boundaries in a variation range of the parameter. The tool as shown is for categorizing a single parameter. The parameter may be measured by the patient, measured by a laboratory or, as will be described below, it may not be a measurement but rather a symptom.

The tool enables the physician to define regions therebetween and to categorize the regions. The tool comprises the following:

1) A visual representation of the variation range as a linear continuum or bar 62.

2) A continuum divider for visually dividing the continuum at user selectable points therealong. The continuum divider preferably comprises a user-selectable number of sliders 66 operable to be moved or dragged by a user to various points he has selected as boundaries between regions calling for different types of response. The number of sliders is selected by the user in accordance with the number of such regions he chooses to define, and 3) A category selector for associating any one of a group of predefined categories with any of the regions. The bar 62 preferably displays each region using a color, typically red, amber or green, which has been pre-associated with the category.

The physician makes use of the bar 62 which appears on his screen 64 and which represents the dynamic range of the parameter being measured. The sliders 66 appear on the sides of the bar 62, which sliders may be moved using a mouse or by selecting the slider and then using arrow keys on the keyboard. Alternatively the sliders may be moved using any other form of user screen interaction equipment, for example using a light pen, touch screen or voice commands. The sliders are moved to define boundaries and then categories are preferably associated with the regions so formed. Colors such as the traffic light colors red, amber and green referred to above may have been pre-associated with the categories and thus the regions on the bar 62 may be displayed using the relevant associated color as described above. Preferably the categories are associated with colors having meanings that the user is likely to associate with the category. For example, if using the traffic light colors then red should be associated with a category requiring urgent action, green with a category indicating no action required and amber with an intermediate category.

In a preferred embodiment, the colors are selectable by the physician. The physician may for example decide not to use the traffic light colors for a patient suffering from red-green color-blindness.

In another preferred embodiment the traffic light colors may be displayed as a traffic light icon 78, enabling the color-blind patient to recognize the color from the position. In one embodiment, free color selection is available to the physician, with the option to choose the use of a traffic light icon in the case of choosing the traffic light colors.

As shown in the drawing, several regions may be given identical categories. In the example illustrated, red regions 68 are shown at both the top and the bottom of the drawing. Amber regions 70 are shown adjacent to the red regions 68 and an inner green region 72 lies between the two amber regions.

In a preferred embodiment, the bar 62 is displayed in association with a graph 76 which shows actual data points of said parameter, scaled to coincide with the scale of the bar 62 itself. The data points preferably come from the patient himself and the measuring system. The graph may be useful in assisting the physician to define regions on the bar 62.

In an embodiment in which the data comes from the patient himself, the graph is useful in allowing the physician to follow recent trends of the parameter vis a vis the patient and to alter the regions in accordance with the monitored trends.

Alternatively or additionally to displaying graphical data, it is possible to display a numerical scale along the bar 62, again to assist the physician in selecting the regions.

It will be appreciated that certain rules may be applied to region formation, for example that red and green regions cannot be adjacent each other but must be separated by an amber region of finite thickness. Again, the rules may be applied by the programmer as global rules or they may be applied by the physician when defining new categories or they may be applied by the physician on a case by case basis. In an alternative embodiment, rules need not be applied at all.

Each region may have labels 74 attached thereto. The attachment of labels is preferably carried out by the physician on a patient-by-patient basis. Labels 74 may be qualitative labels of the measurement such as high, normal and low, and may be accompanied by recommended actions such as "seek physician attention" or "no reaction".

Figure 5A:
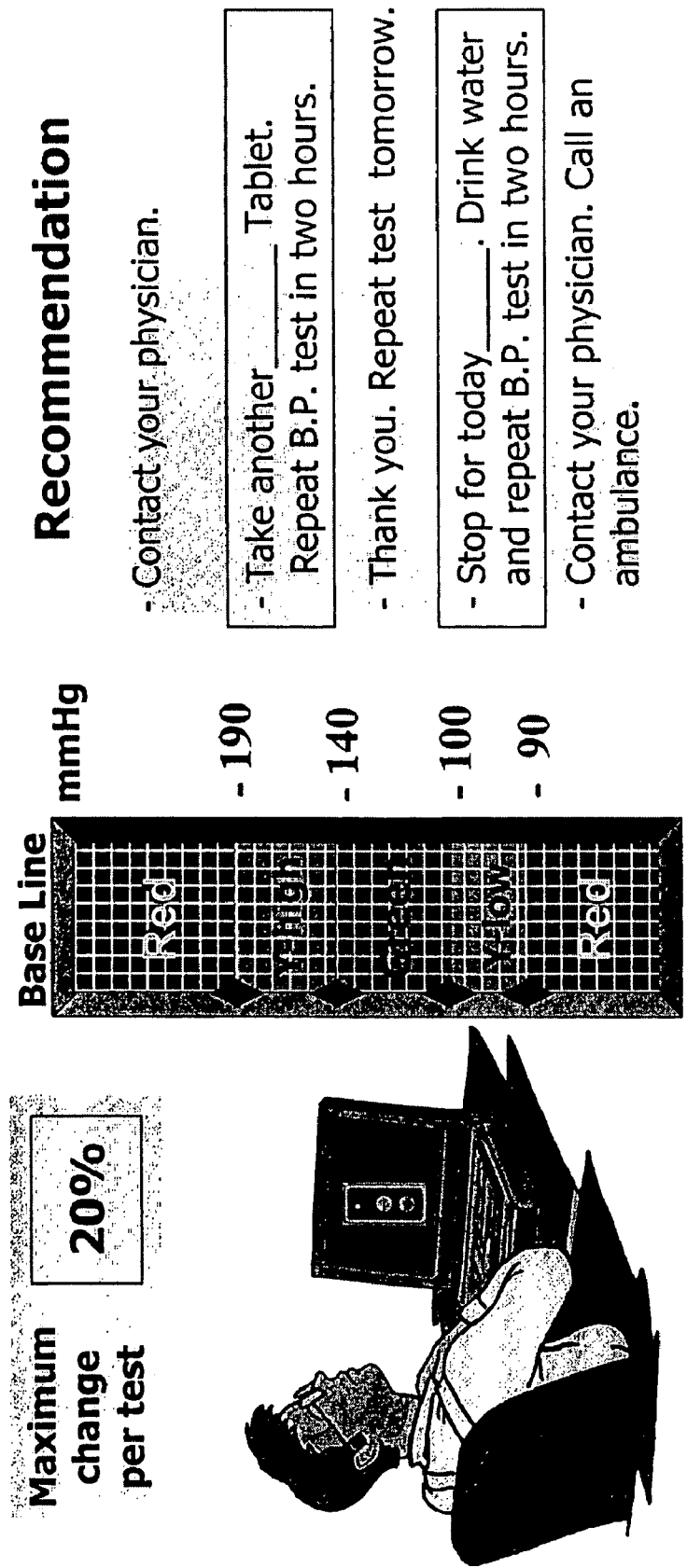
FIG. 5a is a generalized diagram showing a home observation system of a preferred embodiment of the present invention set to monitor systolic blood pressure.

Reference is now made to FIG. 5a, which is a simplified diagram showing how the features of FIG. 4 may be applied to the measurement of systolic blood pressure. Boundaries are, for example, set at 90, 100, 140 and 190 mm of mercury. A green region is recorded between 100 and 140 mm, amber regions between 90 and 100 mm and between 140 and 190, and red regions below 90 and above 190 mm of mercury. A series of recommended actions are shown opposite each region which the patient is asked to follow. Generally in green regions no specific action is recommended other than perhaps to repeat previously defined orders/recommendations by the physician or care provider. In an amber region patient administered treatment is recommended and in a red region physician intervention is called for. It will be noticed that separate regions of the same color are autonomous and need not have the same recommendations.

In the embodiment illustrated, boundary values between the regions are displayed.

A further parameter that the physician may introduce is a maximum change in a parameter. A particular level of a parameter may not of itself give cause for concern but if that level is the result of a very rapid change compared with previous measurements then this may lead the physician to investigate the matter further. The physician is therefore able to introduce a maximum percentage change per test parameter or an absolute change per test parameter. The maximum change may then be given a color category and associated with a recommendation as with the other readings and be treated in exactly the same way.

Figure 5B:
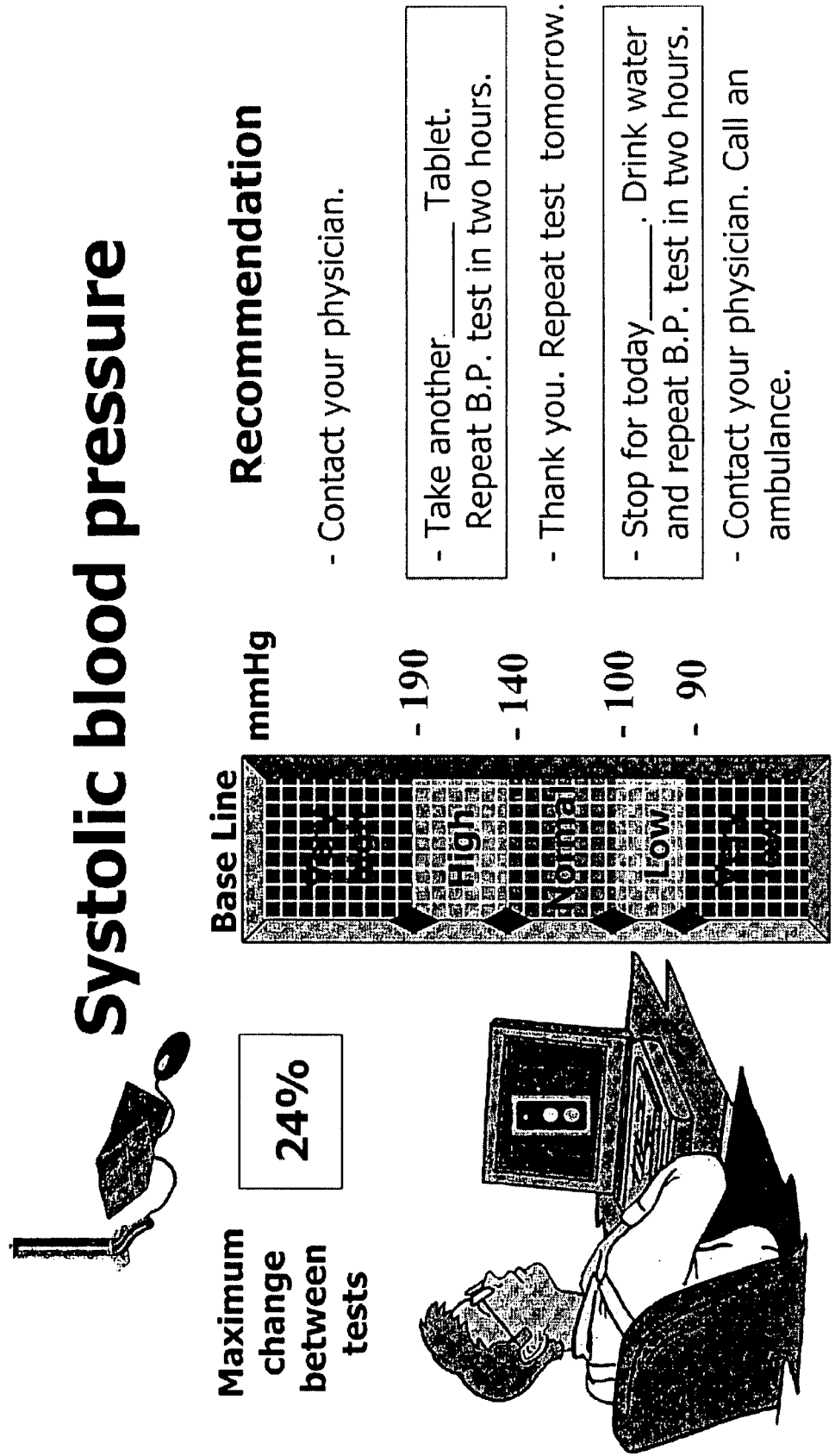
FIG. 5b is a variation of the embodiment of FIG. 5a showing how the same system may be customized differently for a different patient.

Reference is now made to FIG. 5b which is identical to FIG. 5a except that the maximum change between tests is 24% instead of 20%. The higher tolerance may be set by the physician where he is more confident in the patient, perhaps in the case of a younger patient. Either way, this illustrates the point that selection of the parameters is made by the physician on a per patient basis.

Figure 6A:
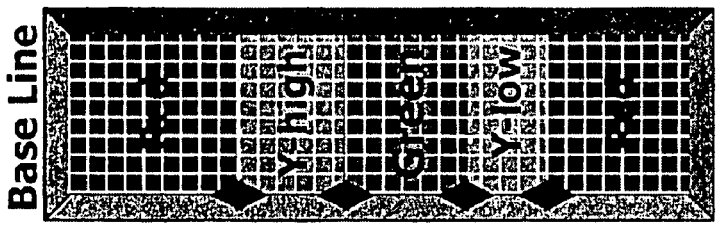
FIG. 6a is a generalized diagram showing a home observation system of a preferred embodiment of the present invention set to monitor diastolic blood pressure.

Reference is now made to FIG. 6a, which is identical to FIG. 5a except that the system has been programmed to measure diastolic blood pressure. The absolute values chosen for the region boundaries are thus correspondingly lower by about 30 mm of mercury but the regions and the associated recommendations are the same. The regions and associated recommendations or actions of course need not be the same, and are preferably set individually for the patient. The maximum allowable change between readings is also unchanged in this example.

Figure 6A:
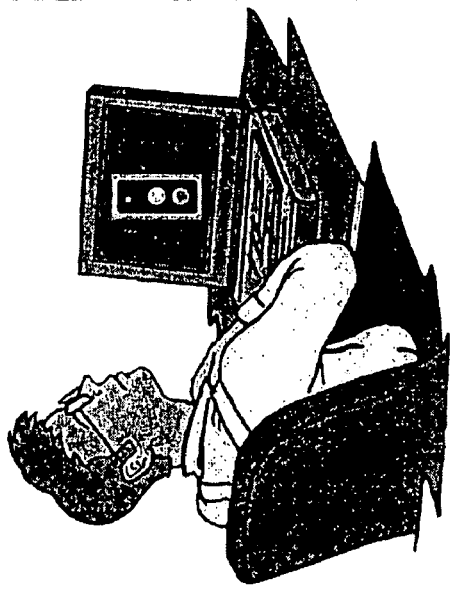
Figure 6B:
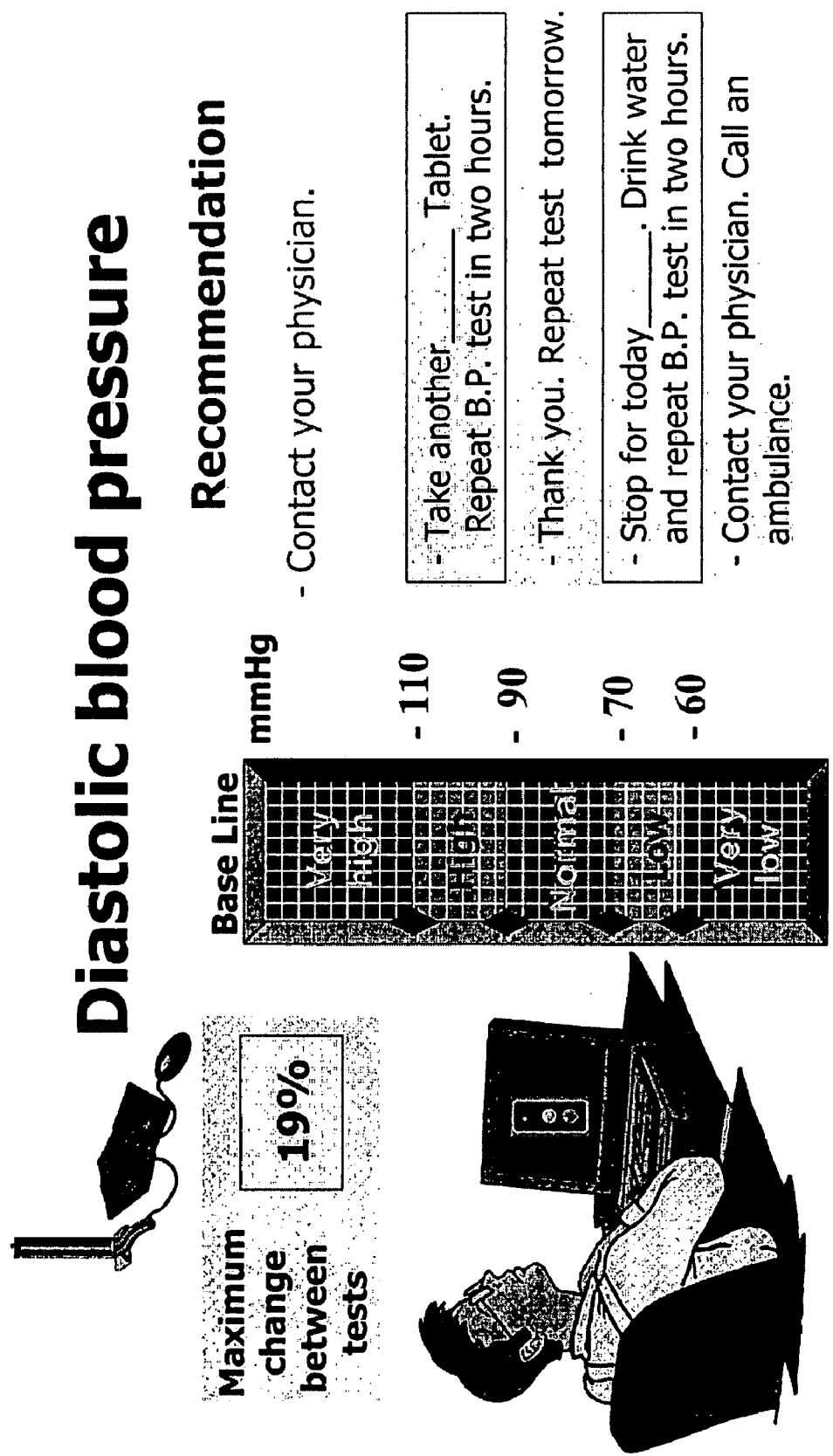
FIG. 6b is a generalized diagram showing how the system of FIG. 6a may be customized differently for a different patient.

Reference is now made to FIG. 6b which is identical to FIG. 6a except that the maximum change between tests is 19% instead of 20%. The lower tolerance may be set by the physician where he is less confident in the patient, perhaps in the case of an older patient. Either way this illustrates the point that selection of the parameters is made by the physician on a per patient basis.

Figure 7A:
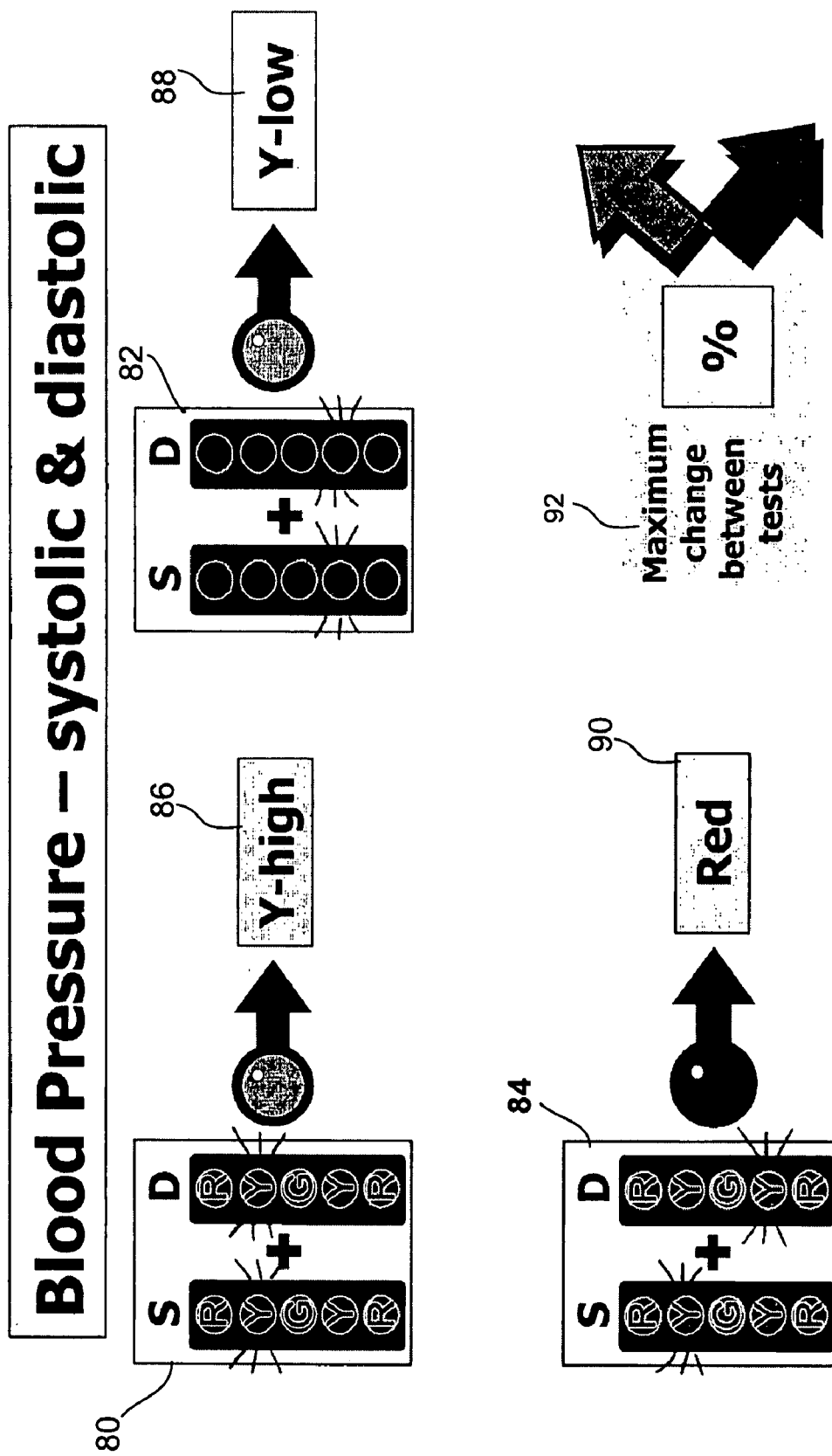
FIG. 7a is a generalized diagram showing a home observation system of a preferred embodiment of the present invention set to combine measurements of both systolic and diastolic blood pressure to produce an output that takes both measurements into account.

Reference is now made to FIG. 7a, which shows how a set of readings may be combined to produce new regions using a simple set of combinatorial rules which are set, preferably on a patient by patient basis, by a physician. In FIG. 7 the two separate systolic and diastolic blood-pressure measurements are each assigned a category as before. Three possible results 80, 82 and 84 are shown. In the first two sets of results, 80 and 82, both the systolic and diastolic blood pressures are shown in the same amber region, that is to say both are in the amber high region 80, or both are in the amber low region 82. The physician defines such combinations as producing a combined result which is either amber high 86 or amber low 88 as appropriate.

If, as in result set 84, one is in the amber high region and the other is in the amber low region, indicating a very large pressure difference, a combined outcome 90 of red is given, even though neither of the individual readings suggests red.

The maximum change between tests is also taken into account as result set 92. If the maximum change between tests is lower than the threshold value set by the physician then the result is green. If the maximum change is larger than the threshold then the result is red.

Figure 7B:
FIG. 7b is a generalized diagram showing the information of FIG. 7a in more concise format.
Figure 7B:
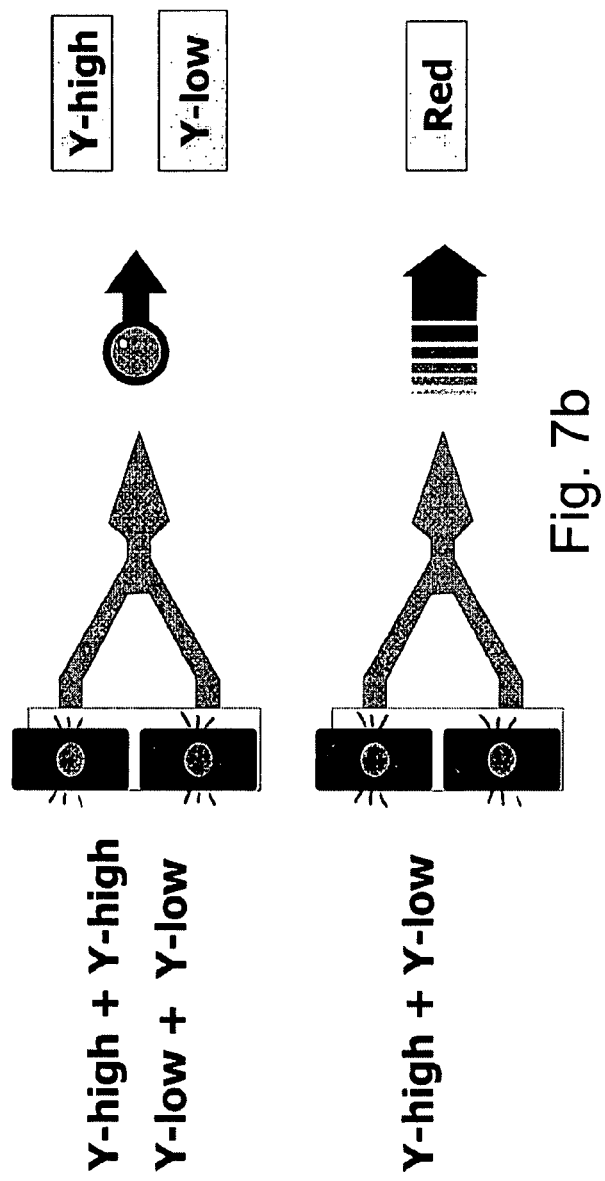

Reference is now made to FIG. 7b, which shows the same information as that in FIG. 7a except that the information is summarized more concisely.

Reference is now made to FIG. 8a, which shows how the same set of measurements may be combined together differently to produce different outcomes, perhaps for a younger patient where the physician is less concerned about complications. In FIG. 8 the two separate systolic and diastolic blood-pressure measurements are each assigned a category as before. Three possible results 100, 102 and 104 are shown. In the first two sets of results, 100 and 102, both the systolic and diastolic blood pressures are shown in the same amber region, that is to say both are in the amber high 100, or both are in the amber low, 102. The physician defines such combinations as producing a combined result 106 of green.

If, as in result set 104, one is in the amber high region and the other is in the amber low region, indicating a very large pressure difference, a combined outcome 110 of red is given as before. However, the physician or care provider may override the red outcome with an amber outcome which he may associate with different orders.

Figure 8B:
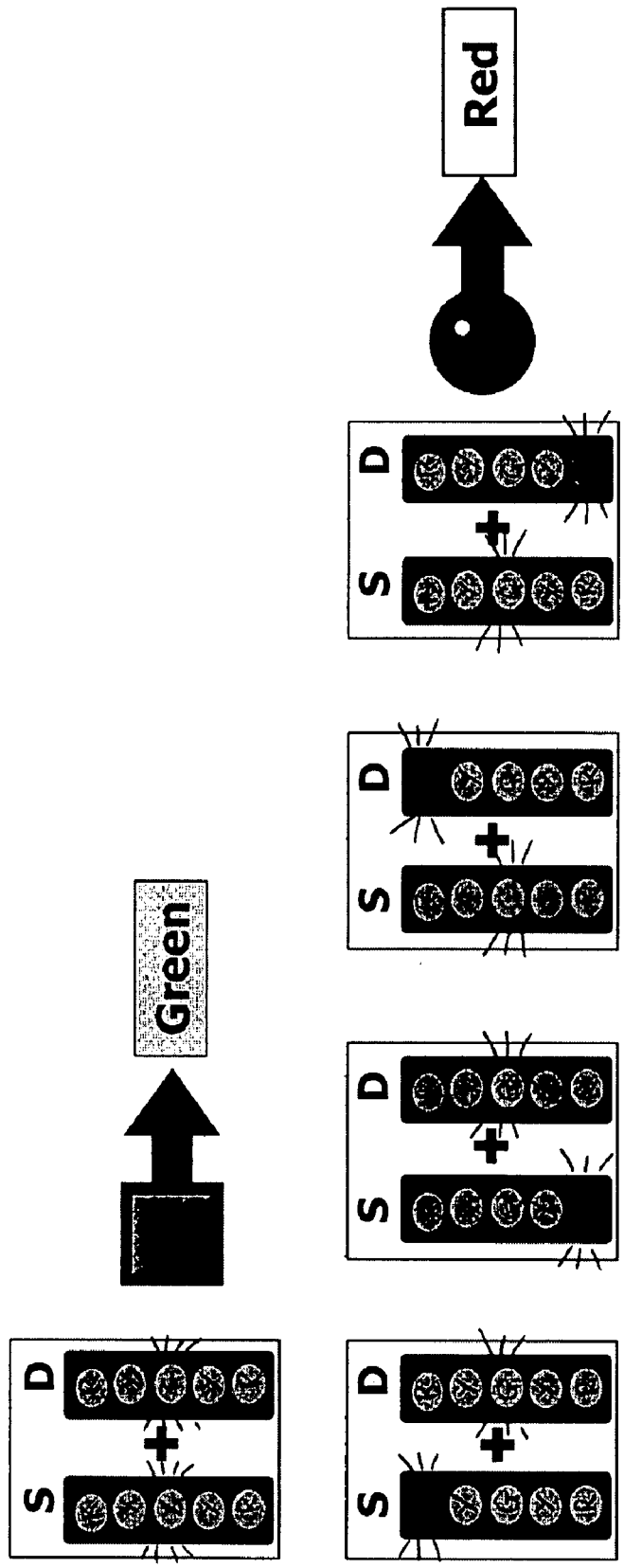

Reference is now made to FIG. 8b, which shows that if two green results are produced, (top row) then the output is green. If on the other hand any of the outputs are red (bottom row) then the overall result is necessarily forced to red.

Figure 8C:
Figure 8C:
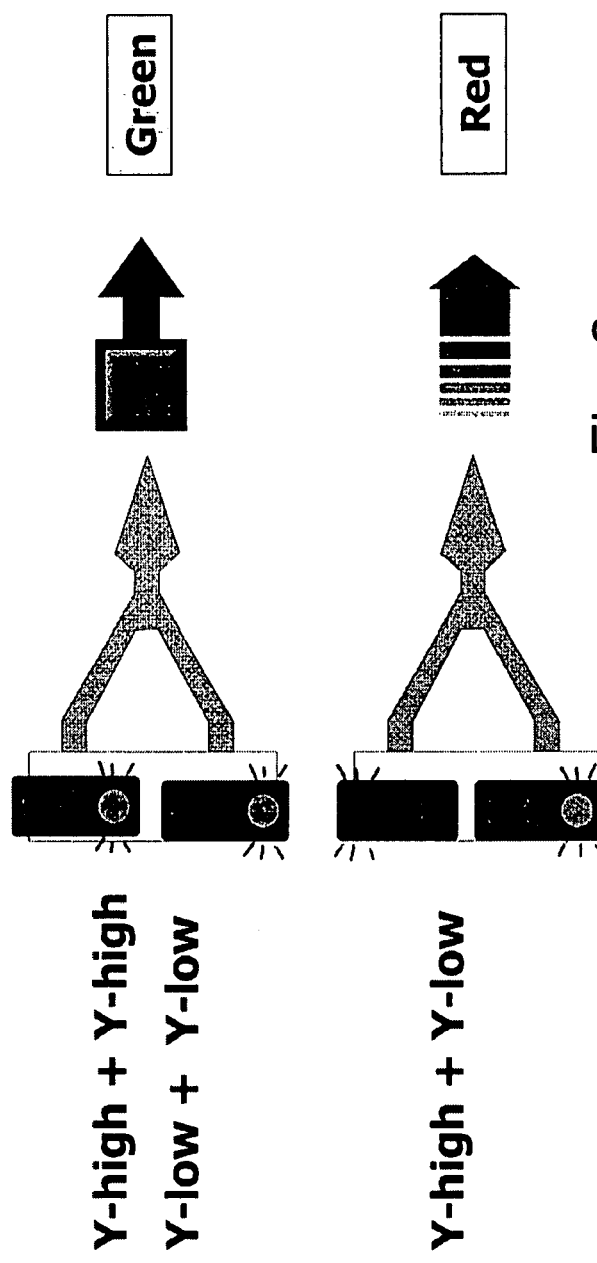

Reference is now made to FIG. 8c, which is a simplified diagram showing the information of FIGS. 8a and 8b in more compact form.

Reference is now made to FIGS. 9a to 9d which are simplified diagrams showing different outcomes of making a series of measurements of weight, blood pressure, heart rate and blood potassium level. The blood pressure may be the individual systolic or diastolic blood pressures or the result of combining the two as described in FIGS. 6 and 7.

As described above with blood pressure, critical boundary levels for all of the above measurements are preferably set by the physician on a patient by patient basis. For example acceptable and non-acceptable body weight is generally perceived as a function of height.

Figure 9A:
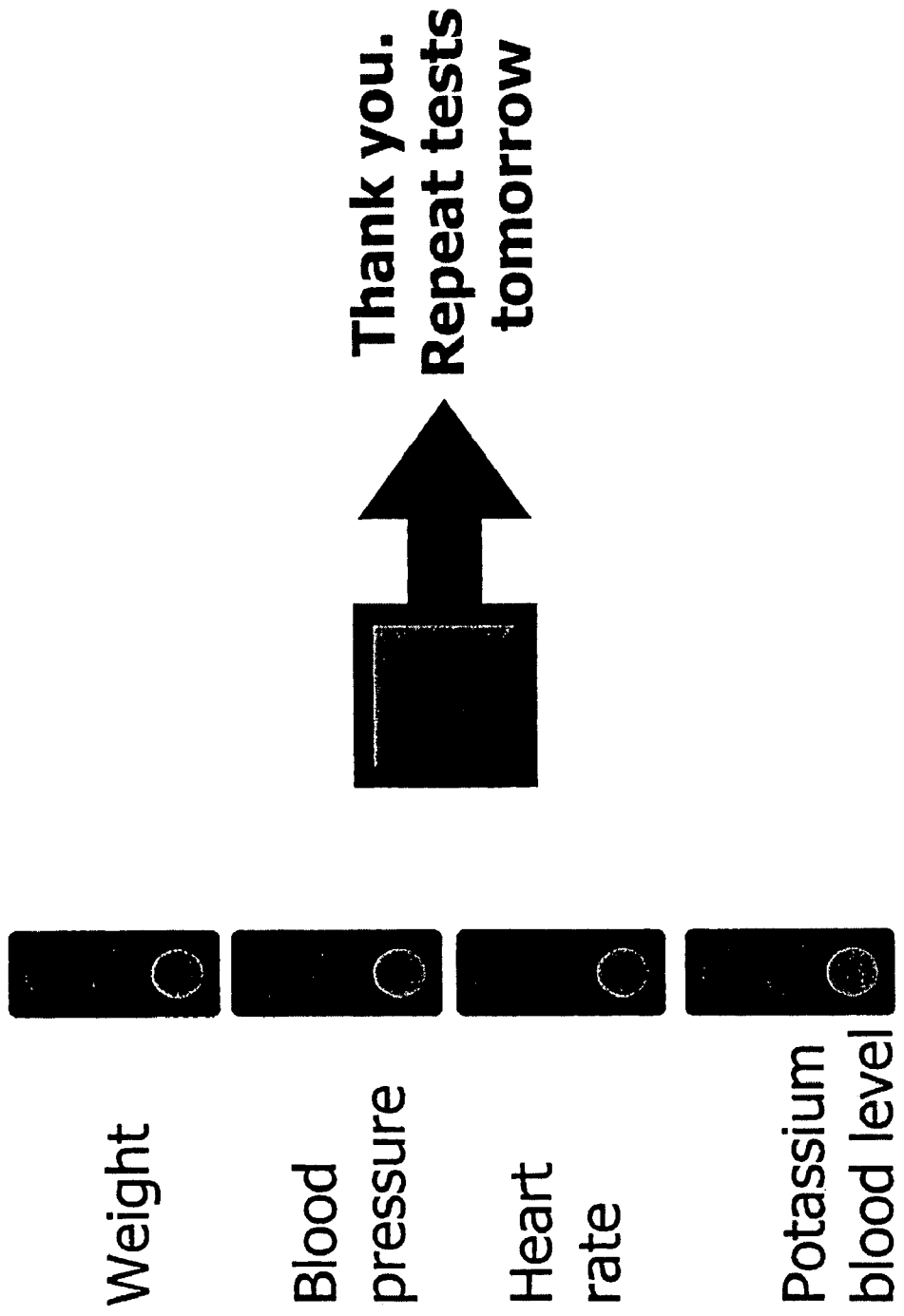
FIGS. 9a to 9d are generalized diagrams showing a home observation system of a preferred embodiment of the present invention wherein different combinations of results of a series of measurements give rise to different output recommendations.

In FIG. 9a all of the tests, that is, for weight, blood pressure, heart rate and blood potassium level, give results which are categorized as green. The patient is simply asked to repeat the tests at a routine interval.

Figure 9B:
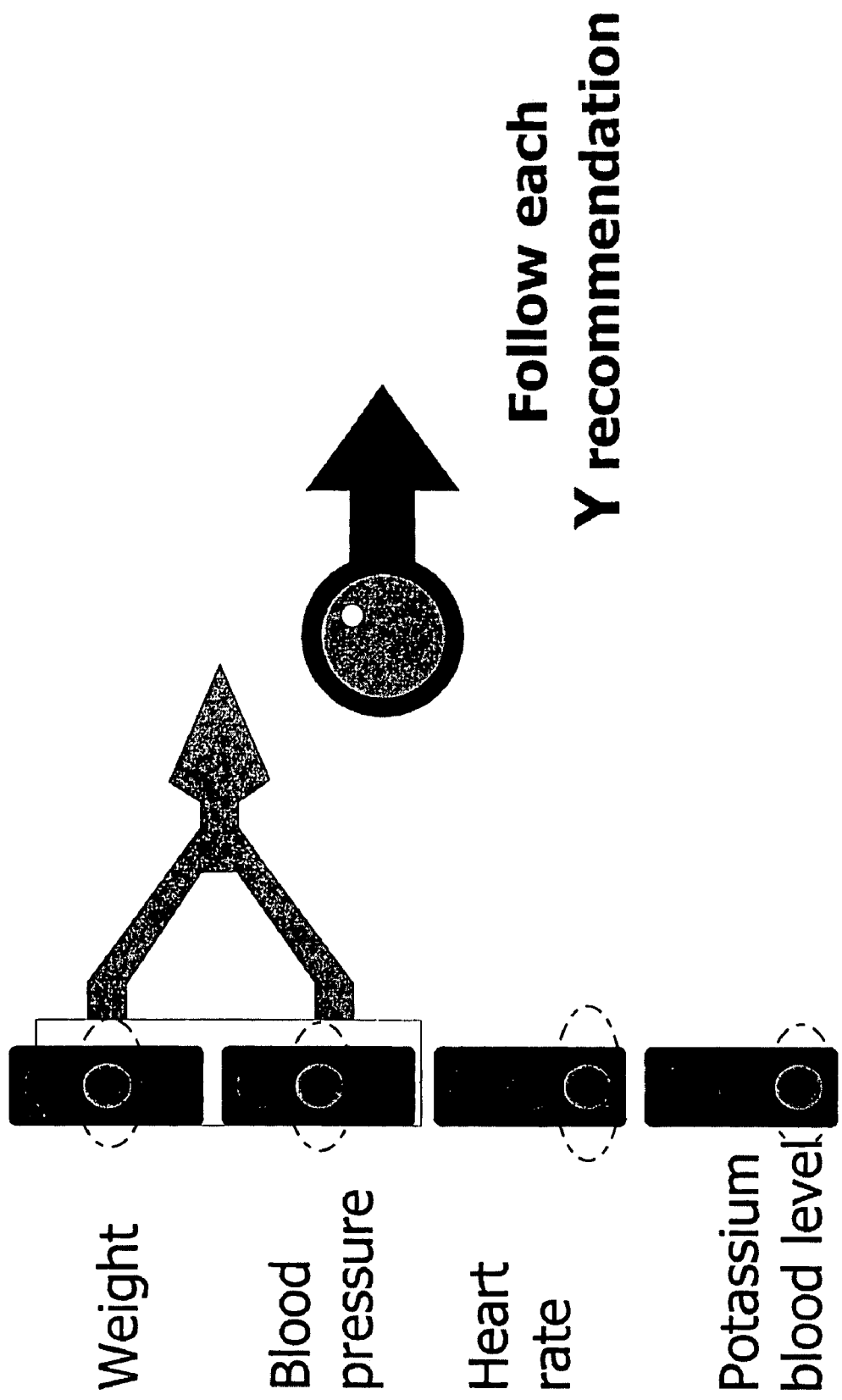

In FIG. 9b, the heart rate and potassium tests reveal normal results which are categorized as green. The weight and blood pressure give amber results which each generate individual order(s) or recommendation(s) but the physician has not programmed any special recommendation for this particular combination of results. Thus the patient is simply presented with the two amber recommendations for weight and blood pressure.

Figure 9C:
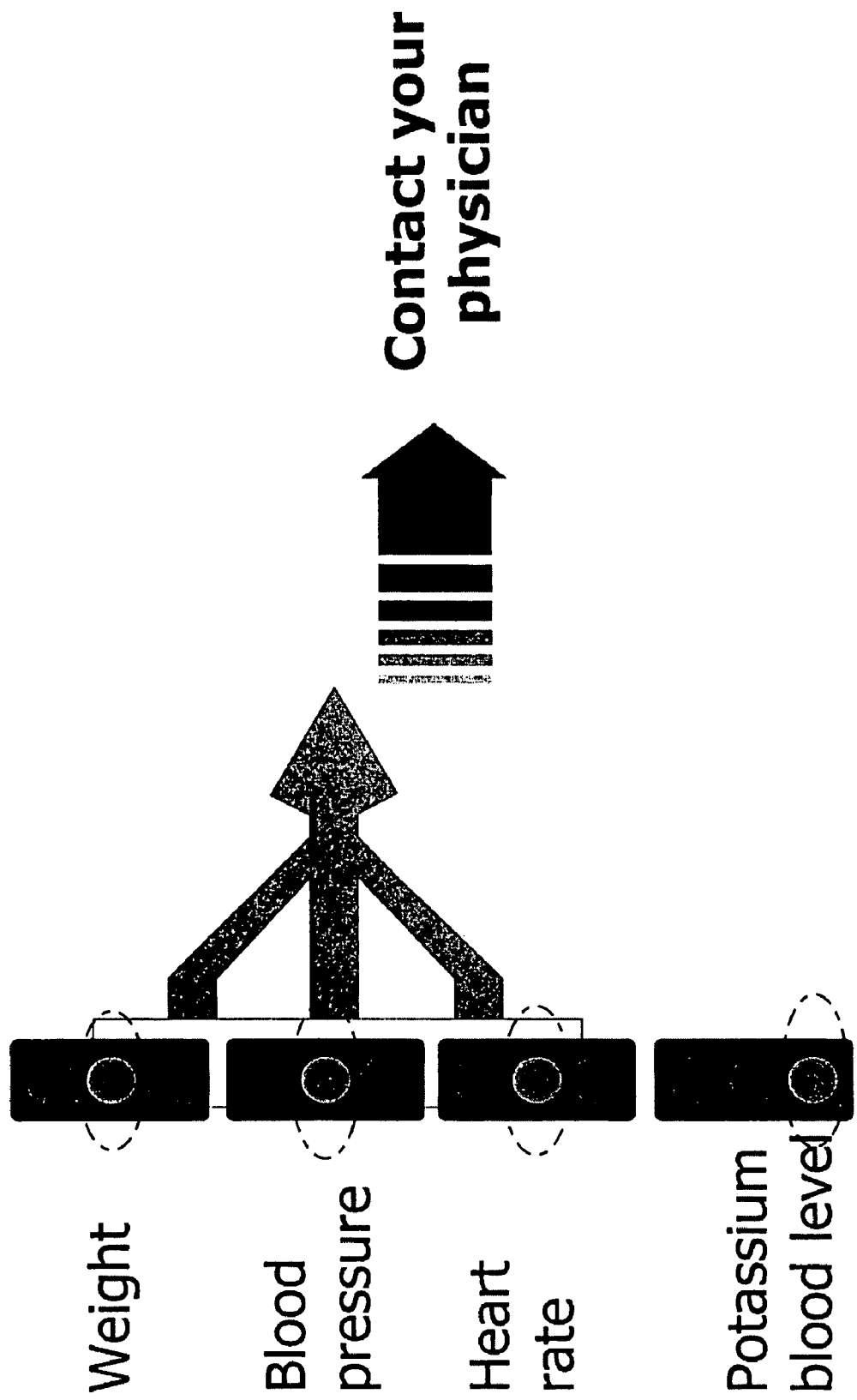

FIG. 9c shows all three of the tests for weight, blood pressure and heart rate returning amber. The potassium test returns green. Such a combination of three amber results has here been set to return an overall red and the patient is advised to contact his physician.

Figure 9D:
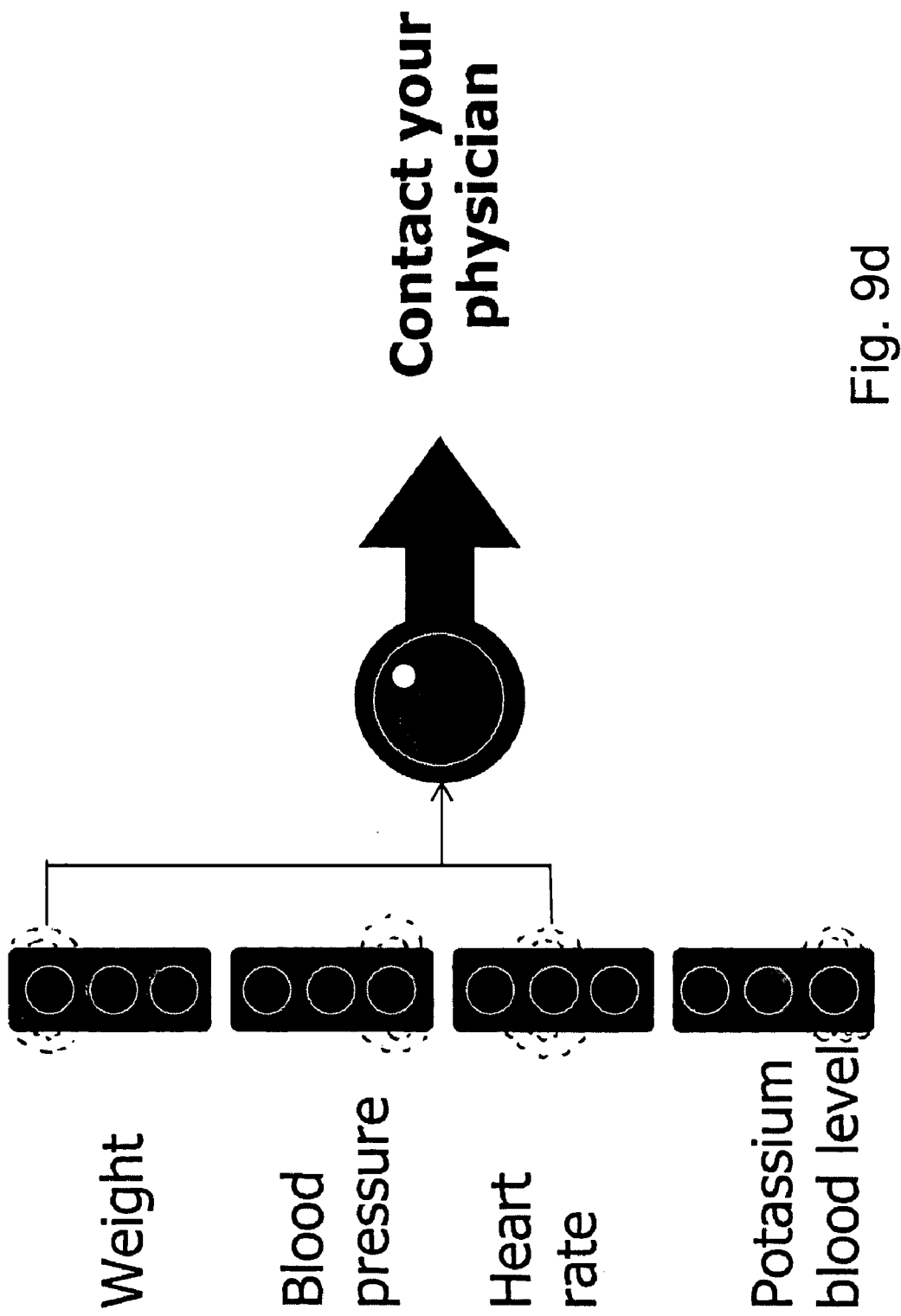

FIG. 9d shows that the weight test has produced a result of red. The blood pressure test and the potassium tests have returned green and the heart rate test has returned amber. In this case, the overall result is red and the patient is once again asked to contact his physician.

Figure 10:
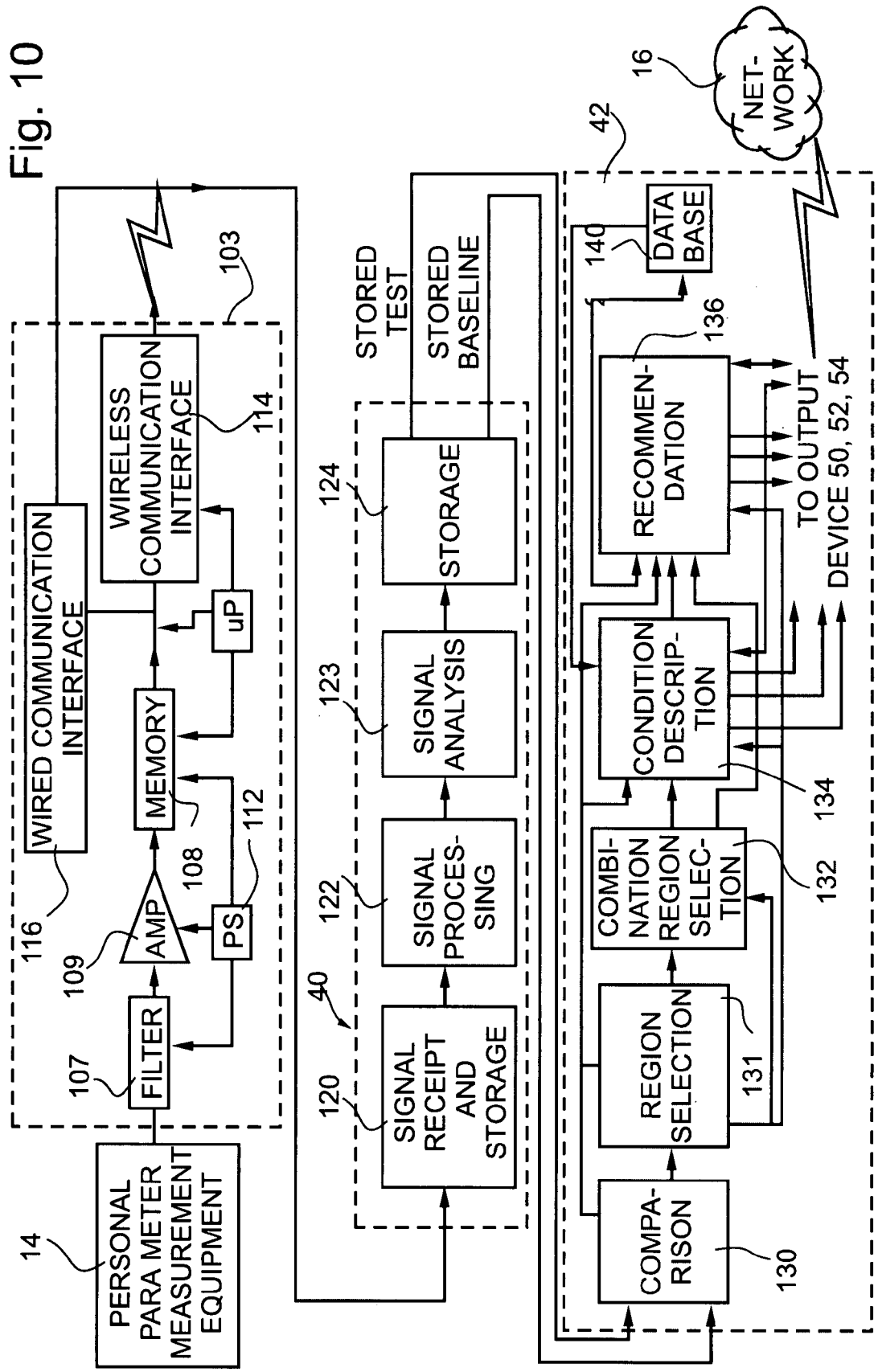
FIG. 10 is a generalized block diagram showing a home observation system of a preferred embodiment of the present invention wherein a measuring device is connected to a data processing device arranged to process measurement data locally into output recommendations.

Reference is now made to FIG. 10, which is a simplified functional block diagram illustration of the general functionality of a data processing device 12 such as a general purpose computer and of an optional personal parameter transfer interface, both forming part of the system of FIG. 2.

In the example shown in FIG. 10, the measuring device, or personal parameter measuring equipment, is directly connected to a data processing device which carries out local processing of the data. As described above, it is also possible for data processing to be carried out remotely, via the network 16.

It is appreciated that the personal parameter transfer interface typically forms part of personal parameter measuring equipment 22 (FIG. 1) and may have different configurations depending on the personal parameter which is sought to be measured and, in certain cases, may be obviated. An example where the interface may be obviated is the hearing testing equipment which may employ a headset. A headset may be connected directly to a general purpose computer incorporating a sound card without requiring any special interface.

As seen in FIG. 10, personal parameter measurement equipment 14, such as a stethoscope transducer, electrocardiogram electrodes and headset, is coupled to optional personal parameter interface circuitry, designated generally by reference numeral 103. Circuitry 103 typically includes one or more of the following components: a filter 107, an amplifier 109, a memory 108, a microprocessor 110, a power supply 112, a wireless communications interface 114 and a wired communication interface 116. Where a memory 108 or a wireless interface 114 is provided, the interface circuitry 103 may be portable and thus particularly useful for emergency applications.

Typically the personal parameter interface circuitry 103 is coupled to a suitable port of a data processing device 12 (FIG. 1), such as a serial port, a sound or game port or a universal port and permits outputs to be supplied to the data processing device 12 for processing thereat.

Recording and storage facility 40 (FIG. 1) may, as an alternative to being associated with the server 32, be provided at data processing device 12 for recording and storing parameters received by the data processing device 12 during at least one test. Preferably, the recording and storage facility 40 comprises signal receipt and storage facility 120, a signal processing facility 122, a signal analysis facility 122 and an information storage facility 124. Optionally, any one or more of the foregoing functionalities may be obviated.

Software which is preferably resident in data processing device 12, provides appropriate signal processing and comparison of parameters received by the data processing device 12 and may apply a series of thresholds to a comparison result, as described above, in order to apply categories thereto. The software typically provides, via data processing device 12, an indication of the applied categories along with a suitable description of the situation which may be accompanied by recommendations for action.

The software typically comprises comparison functionality 130 which may receive information representing stored region boundaries and/or a test and which may provide an output to a category selection functionality 131. A second category selection functionality 132 comprises the rules set by the physician for categorizing combined outcomes, as described above in respect of FIGS. 6 to 9d. A condition description functionality 134 preferably receives information relating to at least one of the stored baseline and the test and may also receive outputs of the comparison and category application functionalities 130 to 132. The condition description functionality preferably provides outputs to one or more output devices such as a user screen as well as optionally via network 14 to controller computer 32 and/or to the associated manned center referred to above.

The condition description functionality may also provide an output to recommendation functionality 136, which preferably also receives inputs from comparison functionality 130 and category application functionality 132.

In accordance with a preferred embodiment of the present invention the general purpose computer 10 may communicate with a remote computer, such as a controller computer 16 (FIG. 1), for obtaining additional reference data and possibly carrying out a comparison between the test data and reference data, thereby to provide further information to the user. Such further information may include a more detailed or precise description of the condition indicated by the test results which may be accompanied by a more detailed or precise recommendation for action. Information received via the network may be employed by the recommendation functionality 136 as well as by the condition description functionality 134.

Communication with a remote computer, such as a server 32 may be initiated automatically by the data processing device 12 via the network 16, for example in response to a red categorization. Communication via the network 16 with the controller computer may also be initiated by a user, at the user's initiative.

Condition description functionality 134 and recommendation/order functionality 136 preferably operate in association with a database 140 which stores acceptable ranges of outputs of comparison functionality 130, normalized for age, weight, height, sex and possibly other characteristics. It may also contain standard personal parameter data, for example normal values of personal parameters for a given user or users. The database information is preferably not directly employed in making decisions, as these should be based only on rules and parameter boundaries entered by the physician on a patient by patient basis.

It is appreciated that any one or more of the functionalities and databases described hereinabove in the context of software 42 may be obviated in a given application.

Communication with a remote computer, such as server 32 (FIG. 2) via the network 16 may be actuated automatically in response to the output of comparison functionality 130, category application functionality 131, 132, condition description functionality 134 or recommendation functionality 136. Thus, when a sensed personal parameter or combination causes a category output of red, which may indicate either an emergency situation or a situation requiring physician intervention, communication is established immediately between the user's data processing device 12 and the server 32 via the network 16.

Communication between the user and the manned center may be via the network 16 and/or via conventional telephone or video-conference facilities.

Figure 11:
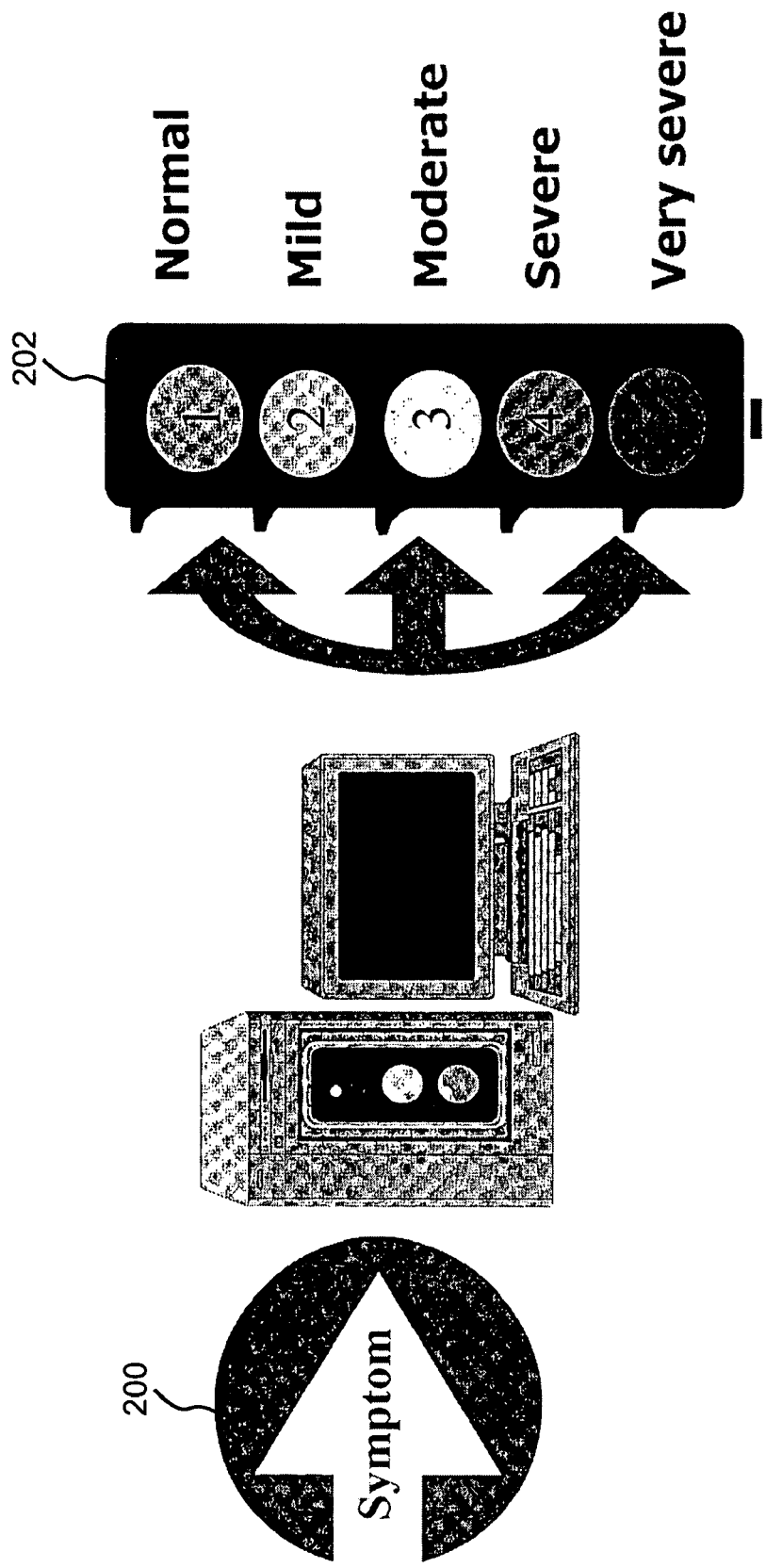
FIG. 11 is a generalized schematic diagram showing how a symptom may be incorporated into an embodiment of the present invention.

Reference is now made to FIG. 11, which is a simplified schematic diagram showing a symptom notification feature which may be incorporated into a home observation system of the present invention. A patient who feels a particular symptom 200, is able to select the symptom 200 and categorize the symptom using various levels of severity 202, for example, normal, mild, moderate, severe and very severe.

In one embodiment the available symptoms are selected by the physician on a per patient basis, so that the patient is restricted to the selection of features that are relevant to his course of treatment. In accordance with another embodiment, the patient may be given a comprehensive list of symptoms to choose from.

The patient typically responds in terms of the selection of categories which are broadly the same for all patients. However, the physician may tailor response levels to his knowledge of the patient. For example a patient with a high tolerance of pain and low propensity to hypochondria, may be assigned higher response levels to lower categories of symptom than other patients.

Figure 12:
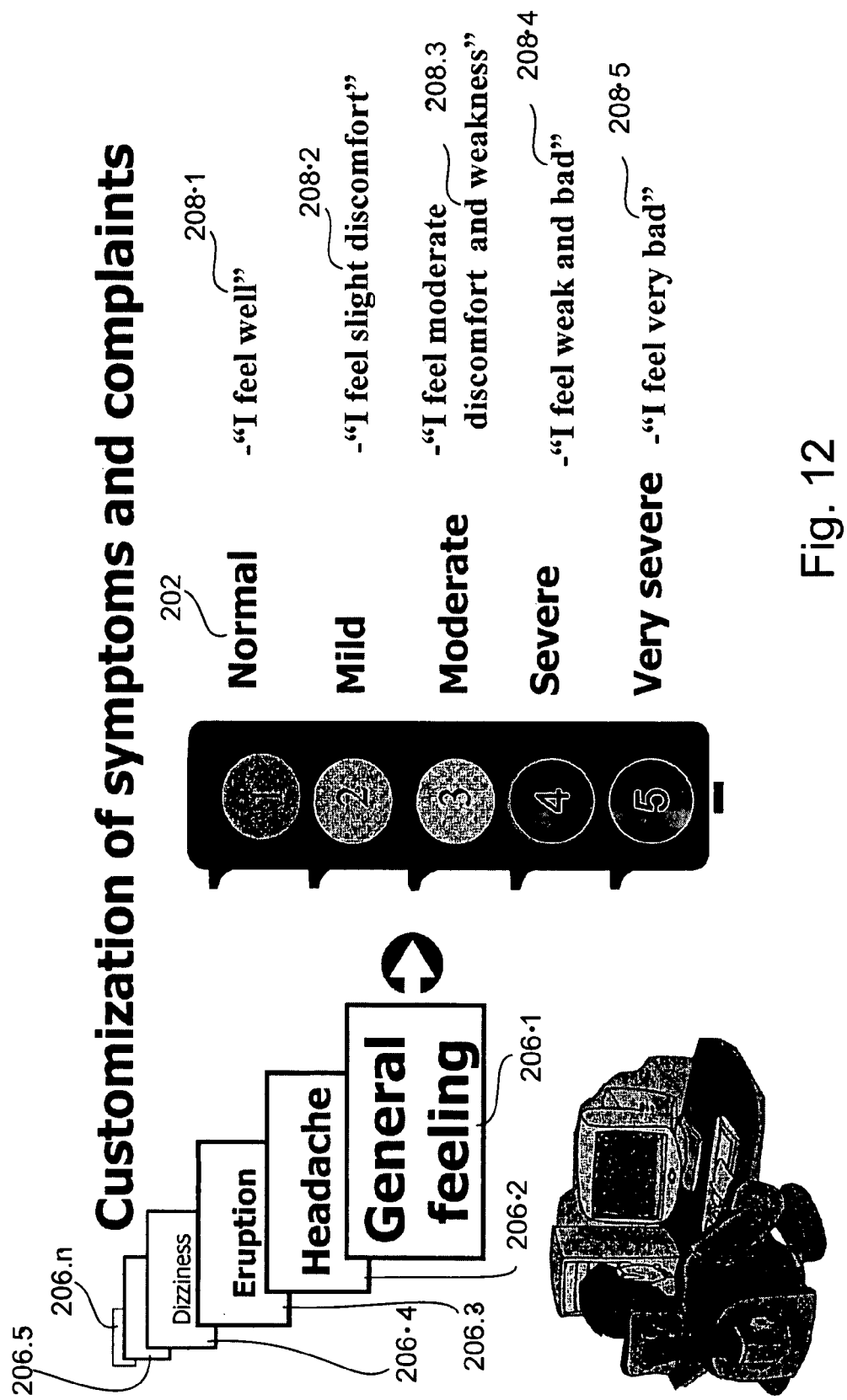
FIG. 12 is a generalized schematic diagram showing how symptoms and complaints may be customized into a home monitoring system on a per patient or per group of patients basis.

Reference is now made to FIG. 12 which is a simplified schematic diagram showing in more detail the symptom notification feature of FIG. 11. In FIG. 12 a series of symptoms 206.1 ... 206.n are selected by the physician, preferably as being relevant to the treatment or condition of the patient. Then a series of response categories 202 are selected as before and each response category is associated with a qualitative statement 208.1 ... 208.5 about the symptom in the language of the patient, which the patient is able to understand clearly and choose from. Typical statements may include "I feel well", "I feel slight discomfort", I feel moderate discomfort and weakness", "I feel weak and bad" and "I feel very bad". The exact content of the statements is preferably selected by the physician on a per symptom and a per patient basis.

Figure 13:
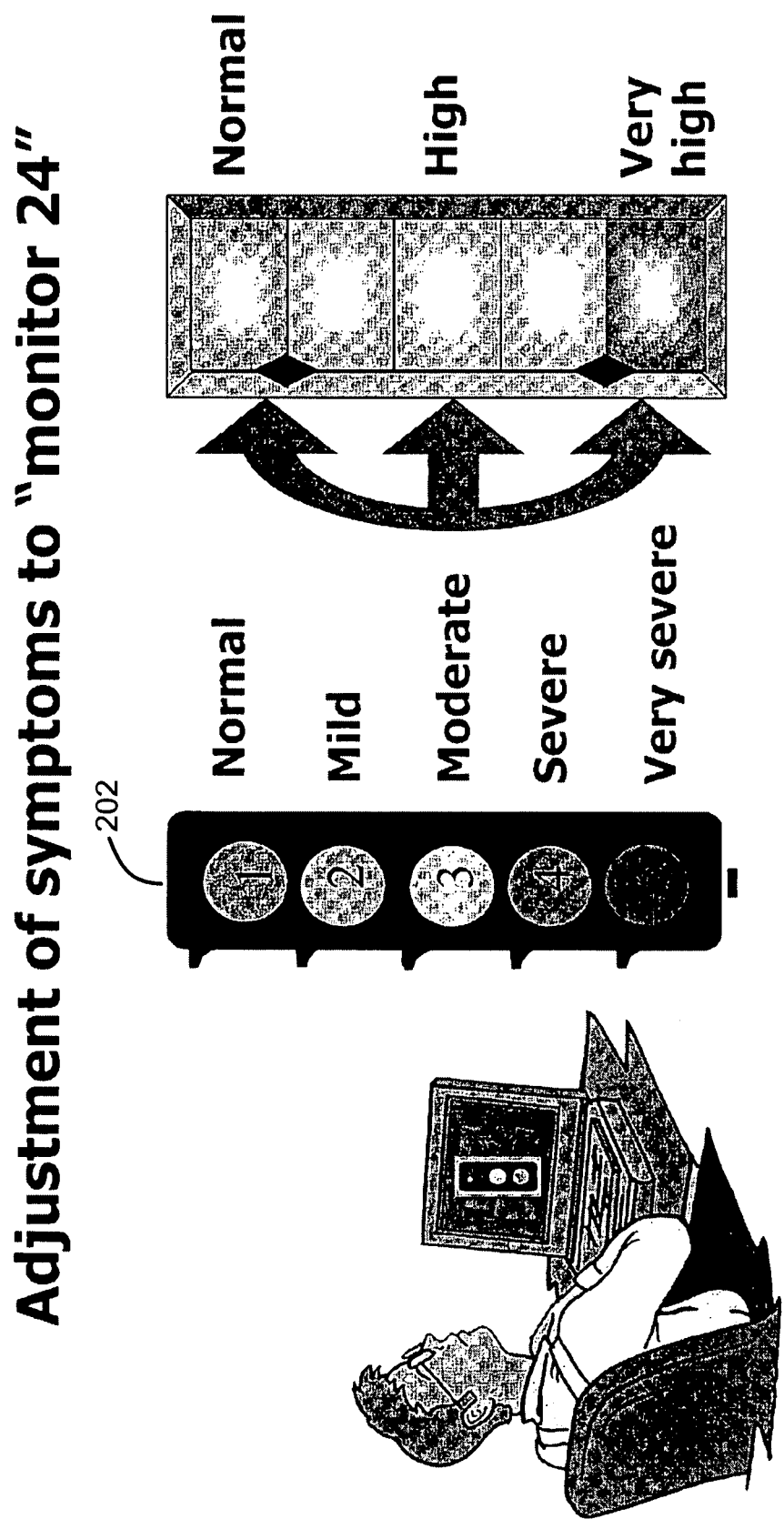
FIG. 13 is a generalized schematic diagram showing how five levels of symptom severity may be mapped onto the three system categorization levels.

Reference is now made to FIG. 13, which is a simplified schematic drawing showing how the symptom notification system may be integrated into a home observation system of an embodiment of the present invention. In the system of FIG. 13, the five categories 202 into which the symptoms were categorized in previous figures are mapped onto the three traffic light colors. The mapping is preferably done by the physician on a per patient and a per symptom basis. In the illustrated example, the normal level is mapped onto green and the very severe level is mapped onto red with the remaining intermediate categories being mapped onto amber. The skilled person will be aware that other forms of mapping or coloring are possible. As described above, the green category indicates that all is well and the red category indicates a situation to be reported immediately to the physician. The amber categories typically lead to advice being given to the patient and only lead to a notification being made to the physician if they are combined with other amber signals which as a combination cause a red categorization to arise.

Figure 14:
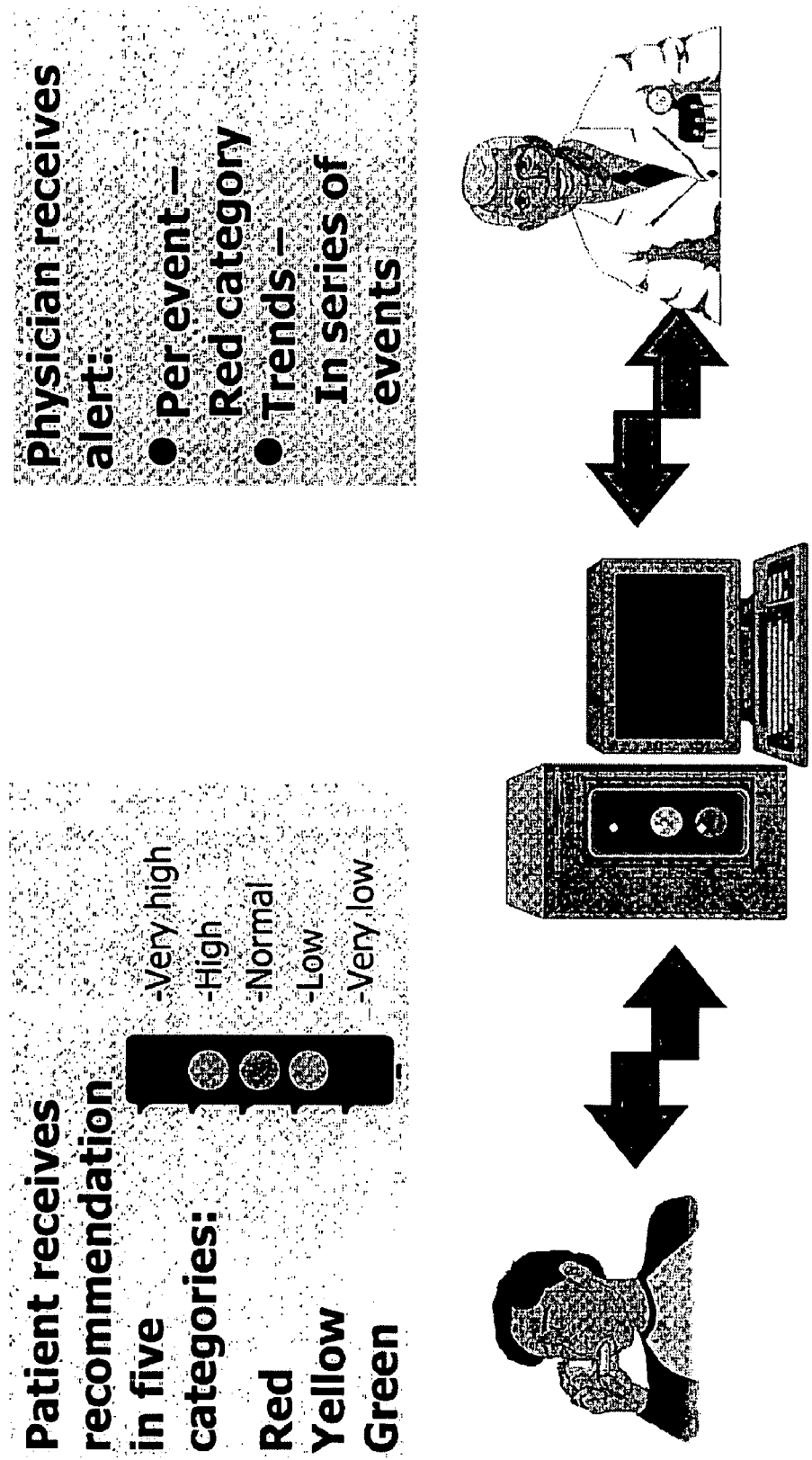
FIG. 14 is a generalized schematic diagram contrasting the way in which a home monitoring system operative according to the present invention reports to a patient and reports to the physician or other care provider.

Reference is now made to FIG. 14, which is a schematic diagram showing how an embodiment of the home observation system communicates with the patient and with the physician, particularly in the case of the symptom notification embodiment. In the system notification embodiment, the patient receives recommendations associated with any one of the five categories 202 with which the symptom has been associated. The fact that the categories were later mapped onto three system categories has no bearing on the first level recommendations made in response to the symptom notification. The three system categories, however, do effect the way in which the symptom notification is combined with other effects to produce secondary categories.

On the other hand the physician receives an immediate alert if any of the recorded symptoms or measurement lead to a red category, either as a primary or a deeper category. The physician also preferably receives regular reports showing trends in the data collected.

Figure 15:
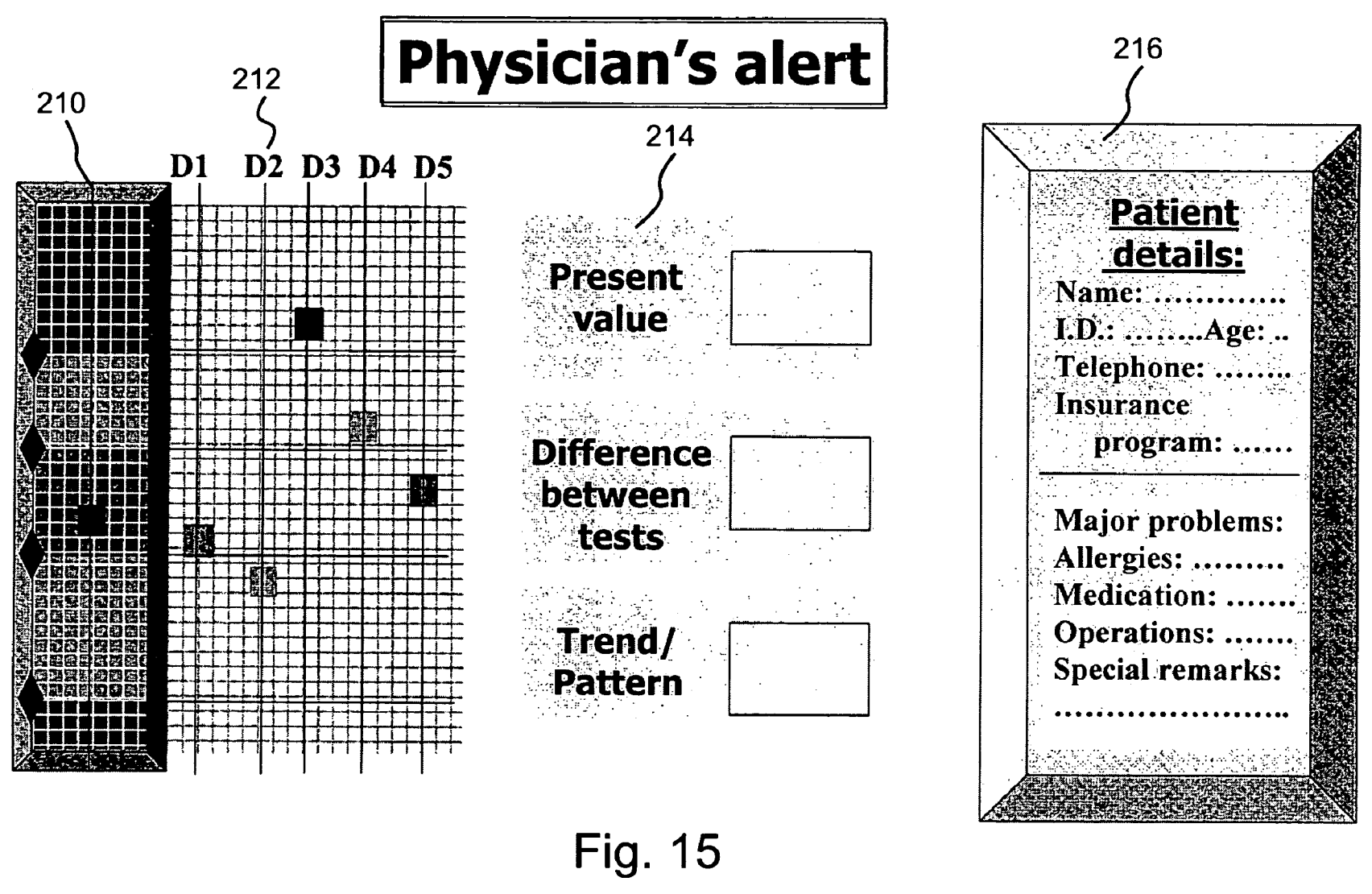

Reference is now made to FIG. 15, which is a schematic diagram showing how a physician may be alerted in the event of a red category or may receive a routine report in the event that there are no red categorizations. In FIG. 15 an indicator bar 210, similar to the parameter value region selection and categorization tool of FIG. 4, appears at the left of the screen. A graph area 212 appears to the right of the bar 210, on which are plotted various data points obtained from the home observation system and from these, the physician is able to identify significant trends. A numerical value region 214 shows various numerical data such as a present value of the parameter, a difference between the present parameter value and a preselected previous value, and a value indicating a trend or pattern. An area 216 to the right of the screen shows patient particulars.

Figure 16:
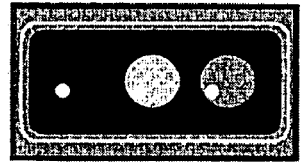
FIG. 16 is a generalized schematic diagram showing in greater detail how a home monitoring system of the present invention is operable to alert a patient to his status.
Figure 16:
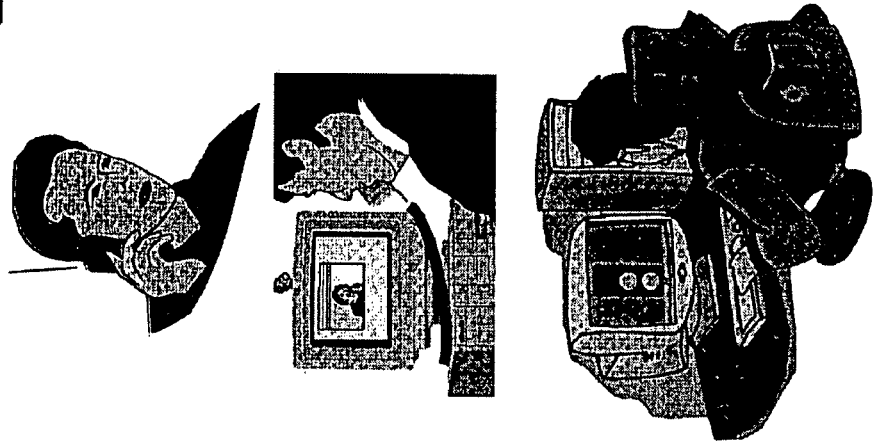

Reference is now made to FIG. 16, which is a generalized schematic diagram showing how patient notification may be carried out in accordance with a preferred embodiment of the present invention. As mentioned above, the content of any particular patient notification depends on the categories 202 associated with each symptom or measurement. However the form of notification and content of the notification preferably fit into the three system categories, such that notifications in the red category are of the nature of "contact your physician" or head for the hospital emergency room" and the like. The amber category contains directions for action to be carried out by the patient and the green category generally contains an indication that routine monitoring is to continue.

Figure 17:
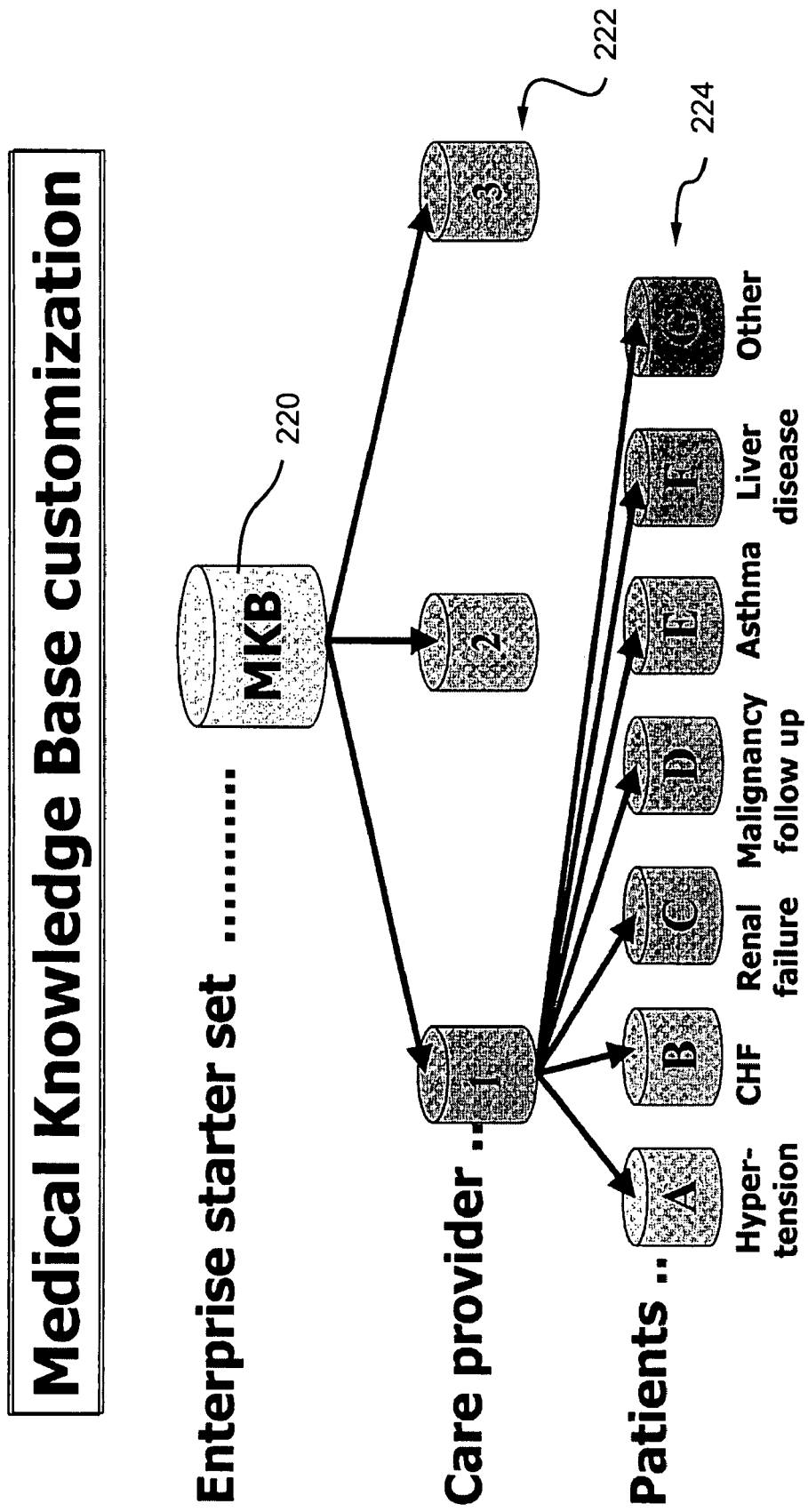
FIG. 17 is a generalized schematic diagram indicating customization levels for a home monitoring system operable in accordance with the present invention.

Reference is now made to FIG. 17, which is a simplified layer chart indicating different layers of customization of an initial knowledge base on which embodiments of the present invention may be based. In FIG. 17, an initial level 220 represents a general system containing the three system categories and the ability to incorporate a large range of parameters to work alone or in combination to produce primary and deeper categorization results. The first level represents an initial starter set of problems to be tracked and recommendations/orders to be associated with different status results and output categories. Typically the starter set knowledge base is predefined at the level of the healthcare organization to form a series of general profiles or templates that allow the monitoring regime to correspond to routine procedures or to after care facilities.

A second level 222 represents a second level of customization that may be provided globally by a care provider such as a physician or a hospital. The physician or the health care provider may use the definitions, profiles or templates defined in the first level or may prepare his own definitions from scratch. The second level allows the physician, hospital etc. to provide a set of more detailed definitions, profiles or templates for specific problems or complaints, that may serve with minimal modification for large numbers of patients.

A third layer of customization 224, at the patient level is preferably carried out by the physician per the specific patient where required. This capability is provided in order to enable the physician to modify the system behavior per each patient, in the context of a specific health care problem being monitored and thus overriding or adding to the general definitions provided in levels 1 and/or 2 as deemed most suitable for each patient.

The physician preferably customizes the system for each one of the different conditions for which he is likely to require monitoring, for example hypertension 224A, CHF 224B, renal failure 224C, malignancy follow up 224D, asthma 224E and liver disease 224F. The physician is also able to program a generic type here labeled "other" 224G which may be used for less routine cases. The system customized for each condition preferably contains the parameters to be monitored, general categorization levels, connections, and significant symptoms such as signs of deterioration or of reaction to the principle drug used in treatment. The system may then later be configured for the individual patient, with precise levels being set for the categorization regions, precise combinations to reach a given secondary results and the like.

Figure 18:
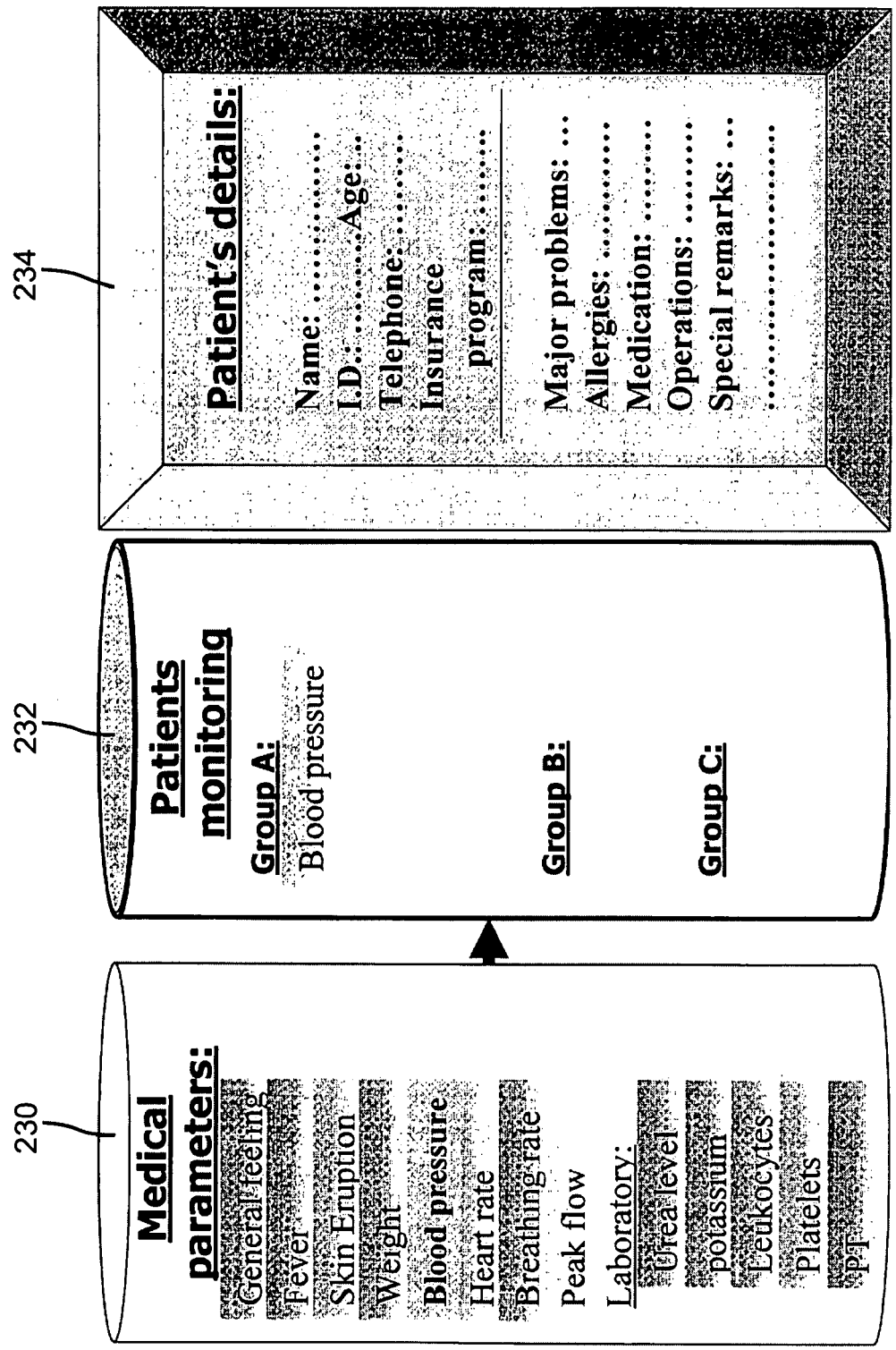
FIG. 18 is a generalized schematic diagram showing a data input form for allowing a physician to customize a home monitoring system on a per patient or per group of patients basis.

Reference is now made to FIG. 18, which shows a series of medical parameters 230 which may be combined in various ways to provide suitable monitoring systems. In the present case, the physician selects blood pressure and copies this to table 232. A form 234 allows him to enter patient record information, either manually or from an associated patient database.

Blood pressure measurement is not a single parameter measurement but rather is a complex of two measurements, diastolic and systolic blood pressure. Thus the physician must set primary and secondary categories for the two measurements in combination. Thus, the physician is invited to set regions of interest in the two parameters of systolic and diastolic blood pressure measurements as discussed earlier in respect of FIGS. 5a, to 6b, and to set relationships between them to establish secondary and consolidated results, as in FIGS. 7a to 8b.

Figure 19:
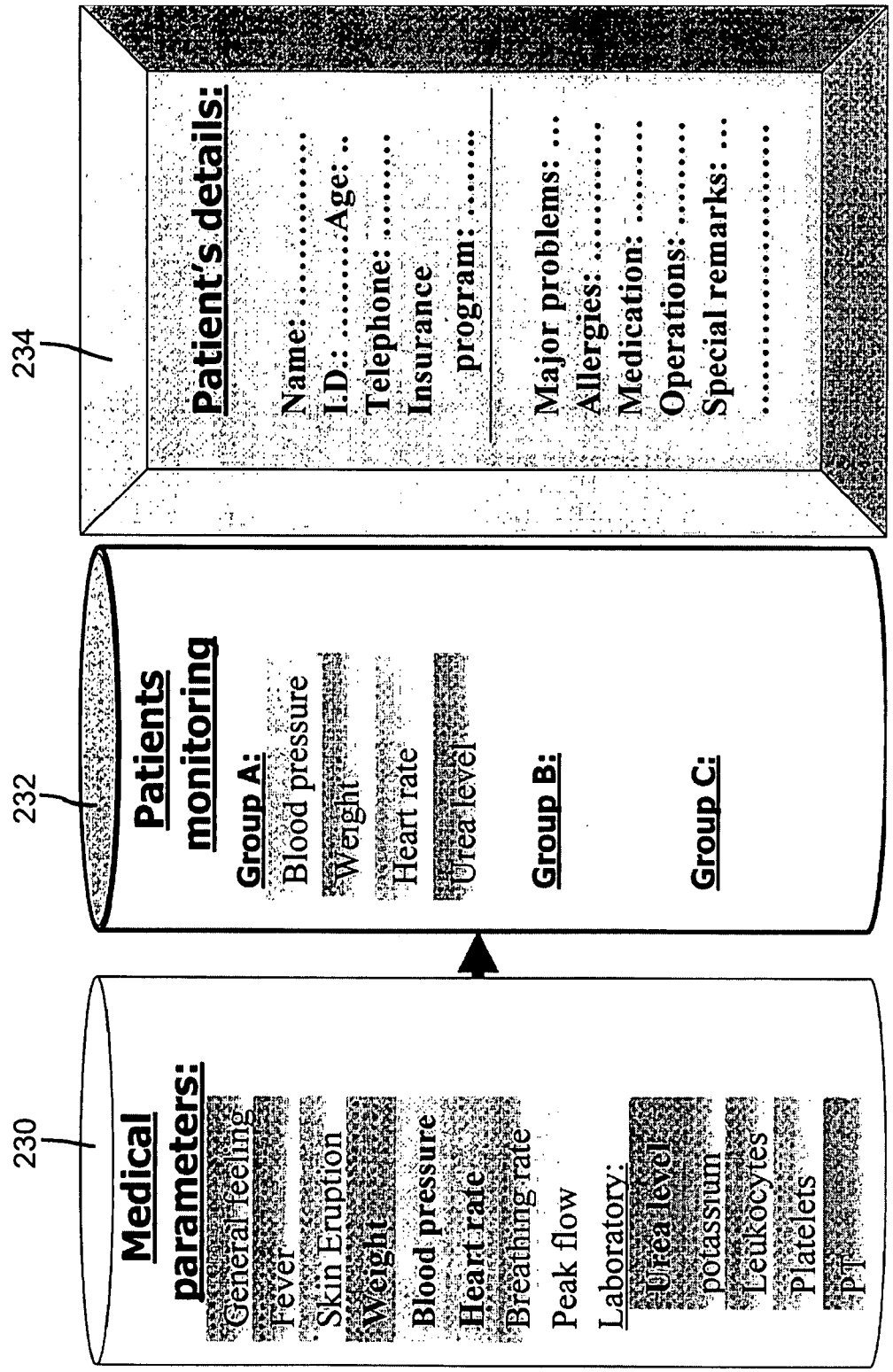
FIG. 19 is a generalized schematic diagram showing the data input form of FIG. 18 at a further stage in customization.

Reference is now made to FIG. 19, which is a schematic diagram identical to that of FIG. 18 except that the further parameters of weight, heart rate and urea level have been added to the parameters to be monitored 232. These parameters are further parameters that it is desirable to measure in the case of congestive heart failure. The further parameters added in FIG. 19 are parameters that, in contrast to blood pressure, generally involve a single measurement.

Reference is now made to FIGS. 20a to 20d which illustrate four rules that can be set for producing secondary categorizations of the results of the four parameters weight, blood pressure, heart rate and urea level. As will be recalled, the blood pressure result is itself a secondary categorization.

Each of the four parameters produces results in one of three system categories, red, amber and green. The three system categories give rise to five actual categories as follows: red high, amber high, green, amber low and red low.

Figure 20A:
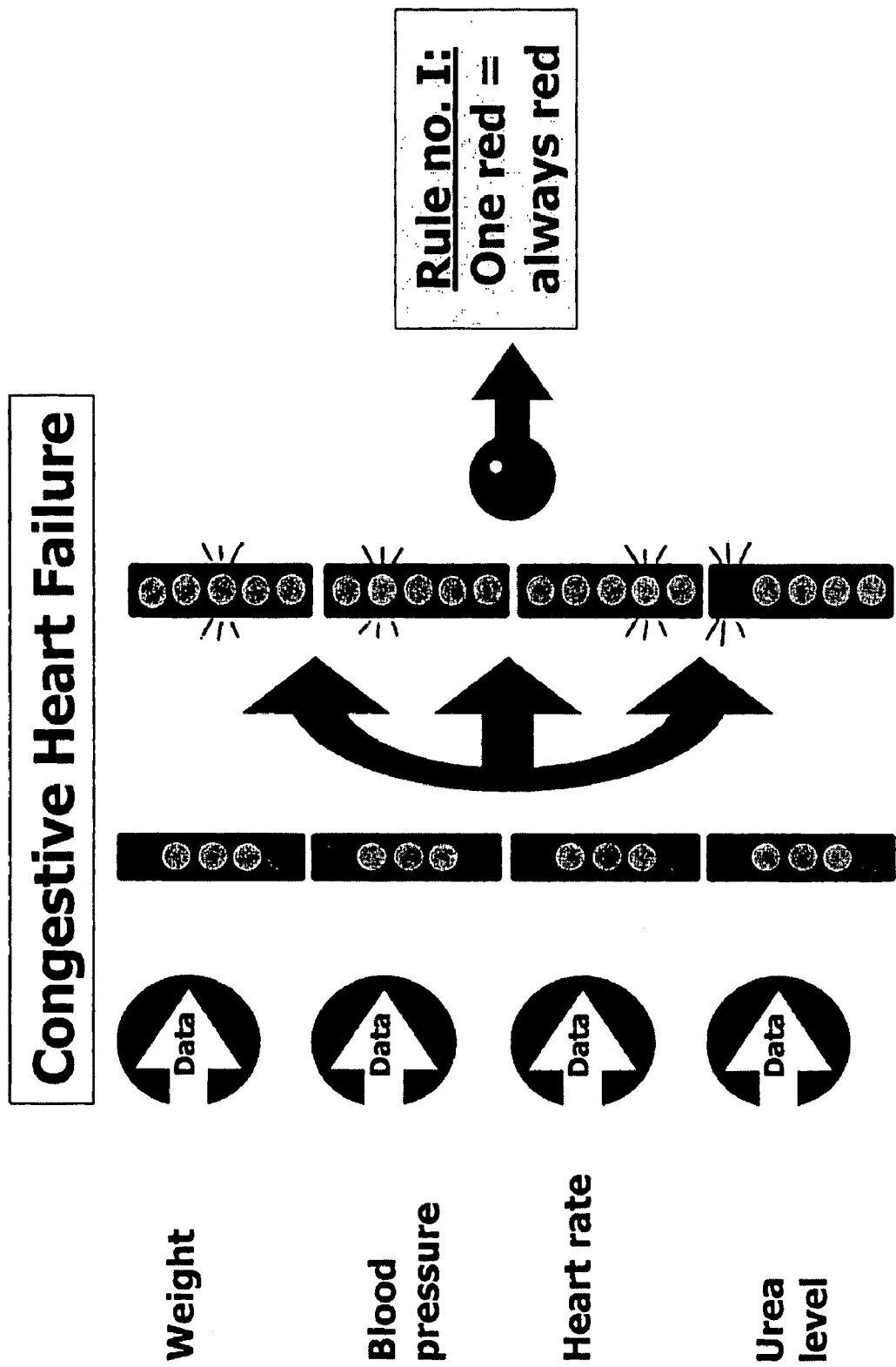
FIGS. 20a to 20d are generalized schematic diagrams showing parameters and illustrating combinatorial rules for producing system outputs from the parameters.

In FIG. 20a, weight gives rise to a green result, blood pressure to an amber high result, heart rate to an amber low result, and urea level to a red result. An overall consolidating result of red is produced by using a rule that states that the resultant category is red if any of the parameters gives red.

Figure 20B:
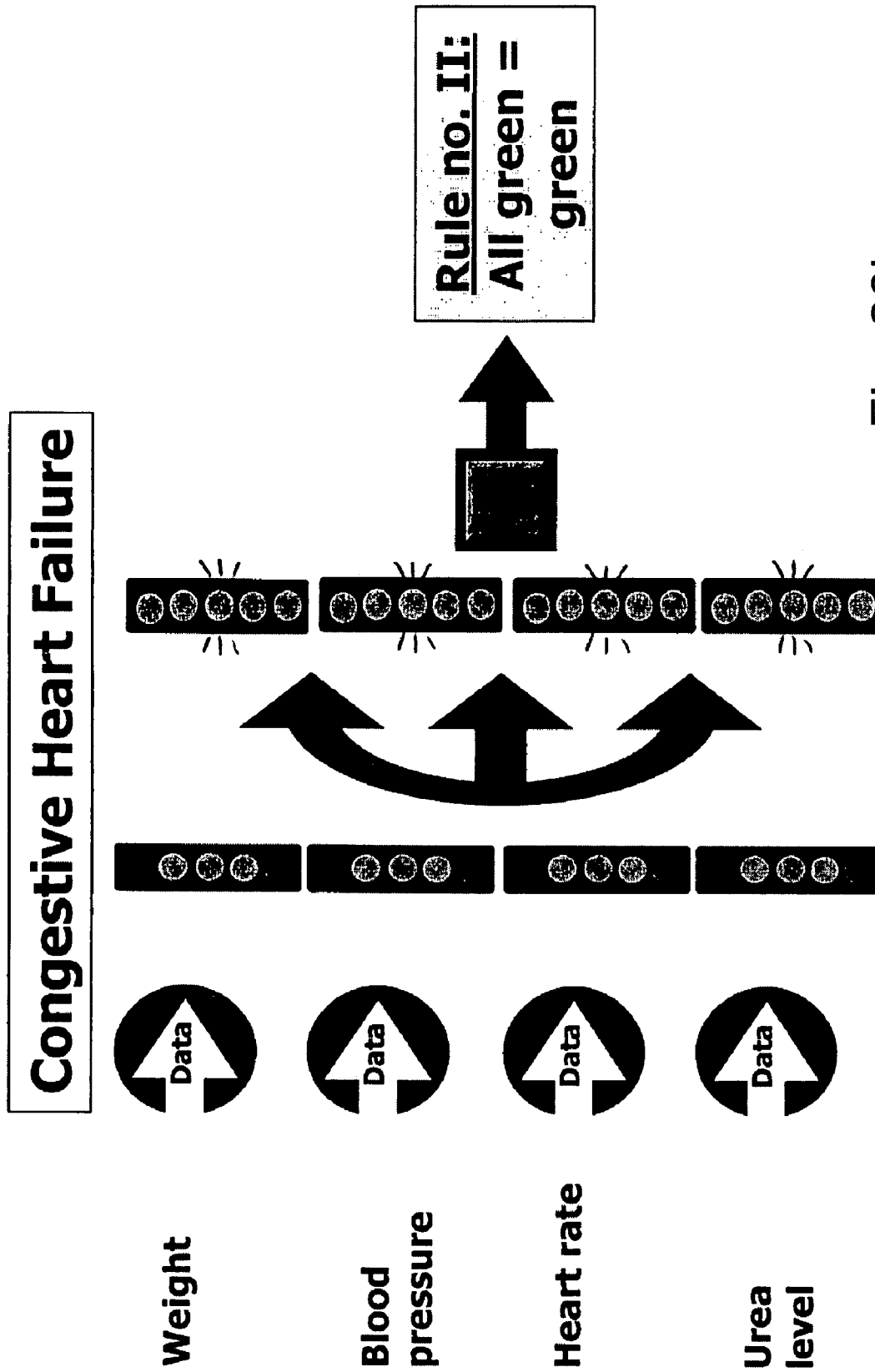

In FIG. 20b, weight gives rise to a green result, blood pressure to a green result, heart rate to a green result, and urea level to a green result. An overall consolidating result of green is produced by using a rule that states that the resultant category is green if all of the parameters are green.

Figure 20C:
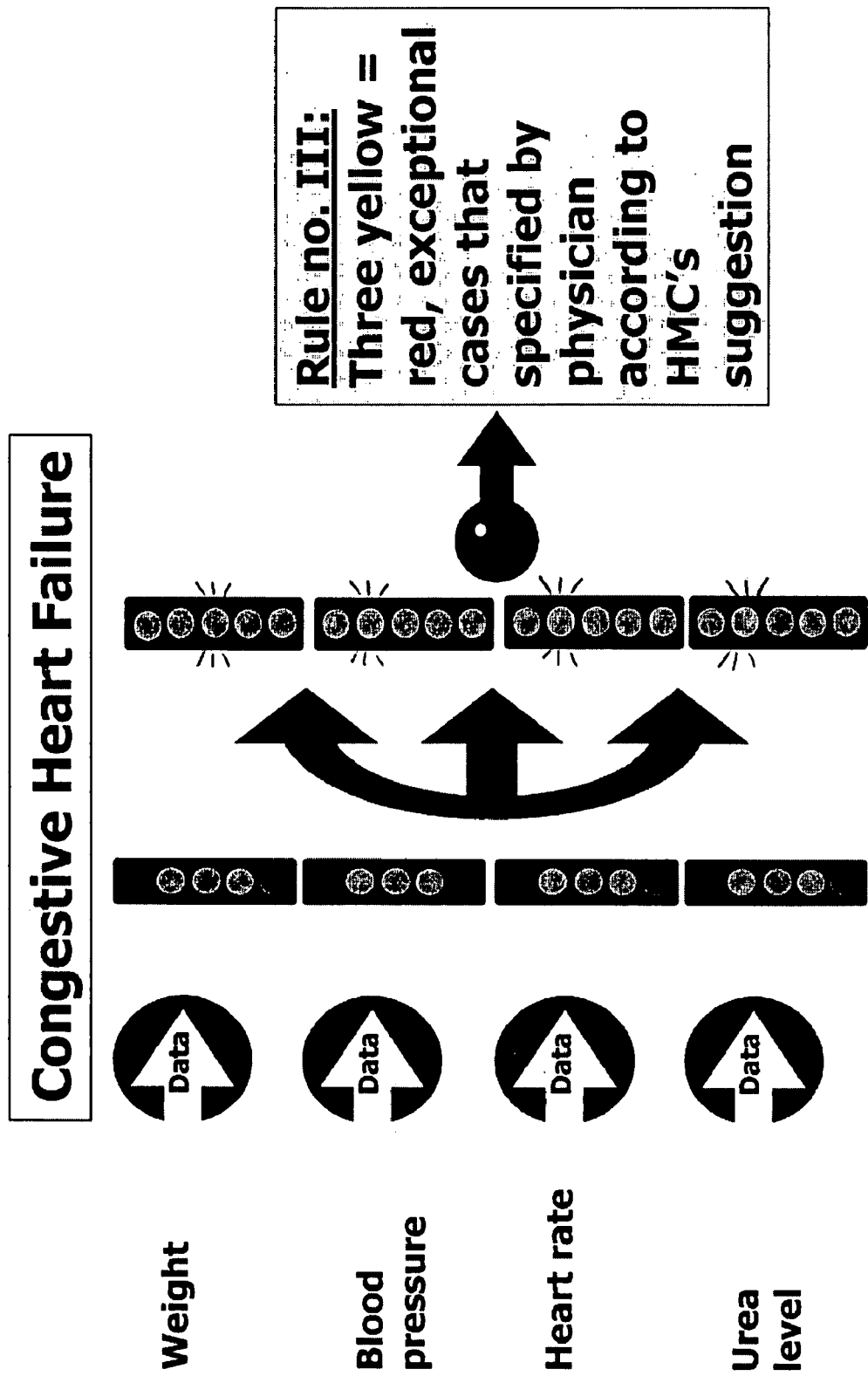

In FIG. 20c, weight gives rise to a green result, blood pressure to an amber high result, heart rate to an amber high result, and the urea level to an amber low result. An overall consolidating result of red is produced by using a rule that states that the result category is red if three or more of the parameters give amber.

Figure 20D:
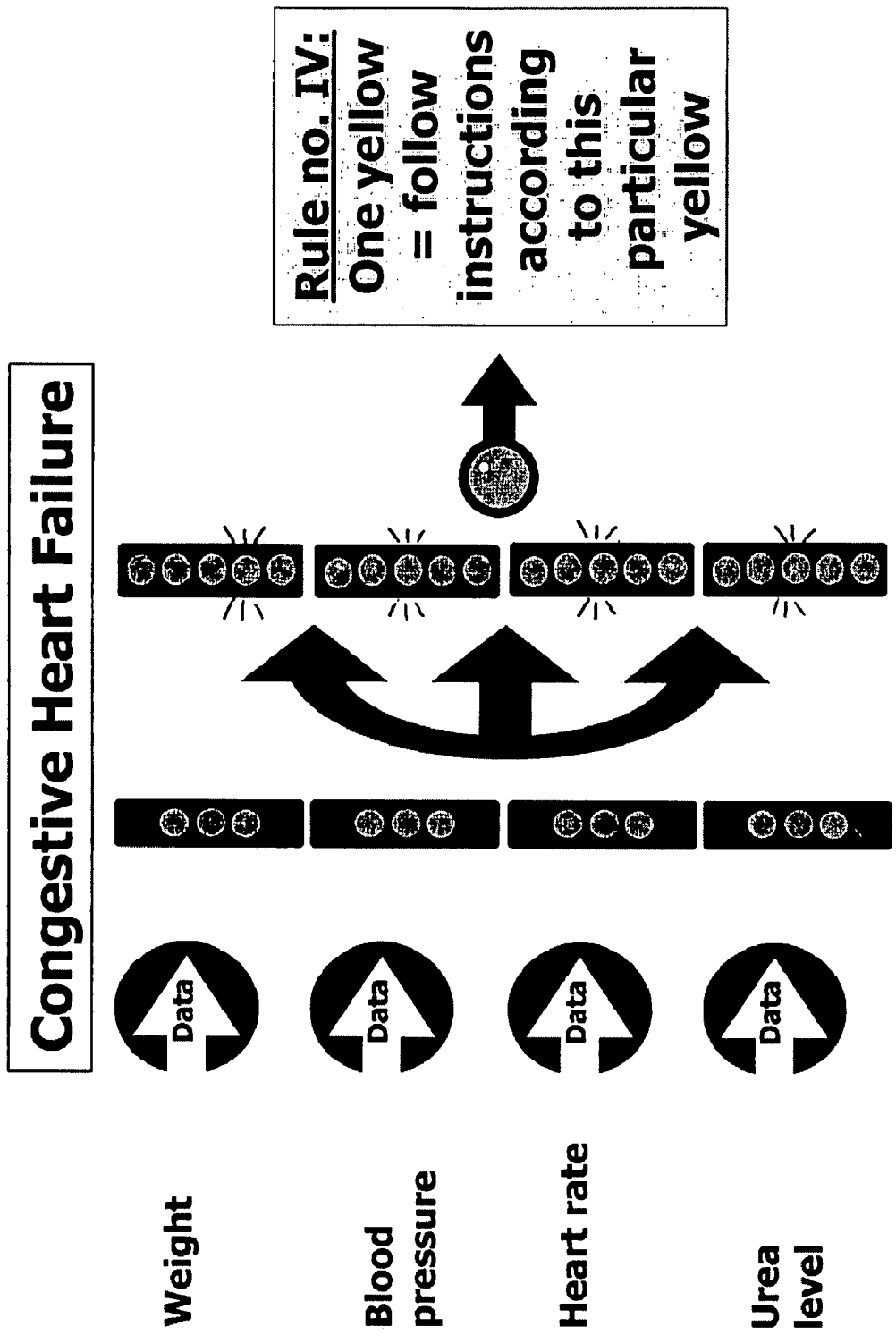

In FIG. 20d, weight gives rise to an amber low result, blood pressure to a green result, heart rate to a green result, and the urea level to a green result. An overall consolidating result of amber is produced and the patient is given instructions that have been associated with the primary amber.

The use of the above rules saves on programming individual combinations. As will be appreciated, when using four or more parameters the individual numbers of combinations can be quite large. However, using rules of this type may mask the behavior of certain parameters by treating them in the same way. Thus, as a further variation, it is possible to sign a parameter, as will be explained below.

Reference is now made to FIGS. 21a to 21d which are simplified schematic diagrams of the way in which the same set of rules may be applied to a set of parameters one of which is signed.

Figure 21A:
FIGS. 21a to 21d are generalized schematic diagrams showing parameters and illustrating combinatorial rules for producing system outputs from the parameters.
Figure 21A:
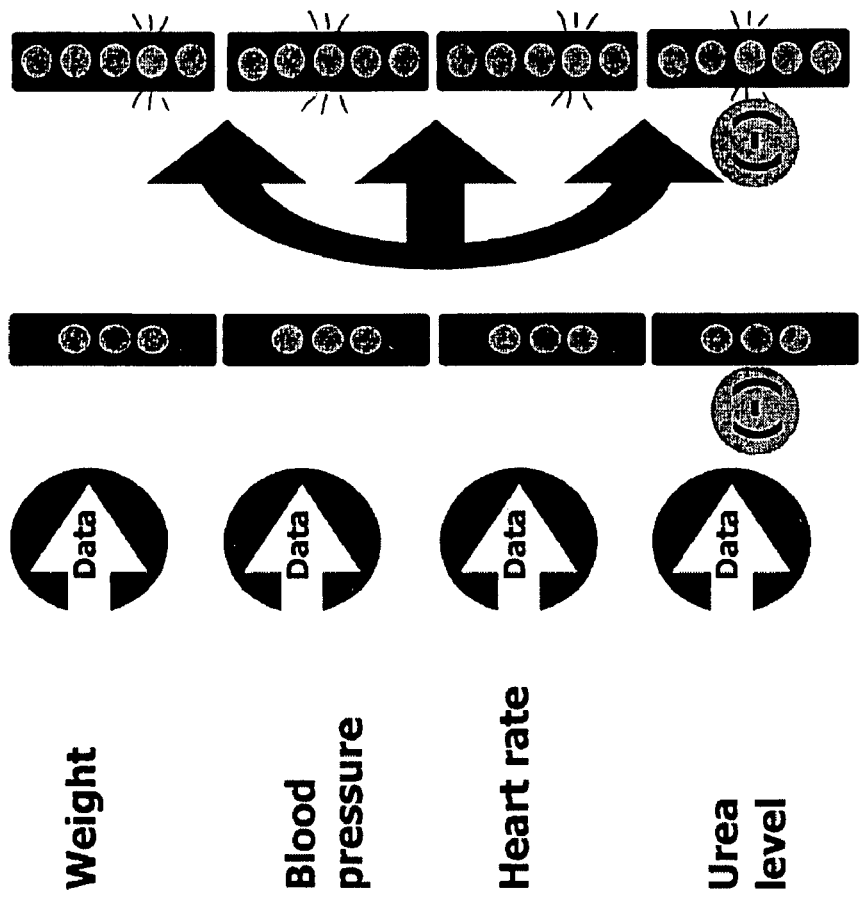

FIG. 21a shows the same set of parameters given in FIG. 20a except that the urea level parameter is signed. In FIGS. 20a to 20d two amber categories led to individual instructions for each amber without giving rise to any combined new category. As was shown in FIG. 7, an amber high category may be set to combine with an amber low category to produce a red. The use of this rule therefore depends on the polarity of the parameter. The polarity of the urea level parameter is important because an amber high represents a situation in which there is a high concentration of urea in the blood due to low levels of fluid in the bloodstream. This could be because fluid aggregates in the lungs or in the kidneys. On the other hand a low concentration of urea in the kidneys represents a high level of fluid in the blood. This could indicate renal failure. Thus the two amber signs mean very different things, need to be treated in different ways and need to be combined in different ways with the other symptoms.

In FIG. 21a, weight is shown as a low amber result, blood pressure as a green result, heart rate as a green result, and urea level as a low amber result. The two amber results, being both low ambers, do not trigger a red result, and the final consolidated output is simply the two amber recommendations.

Figure 21B:
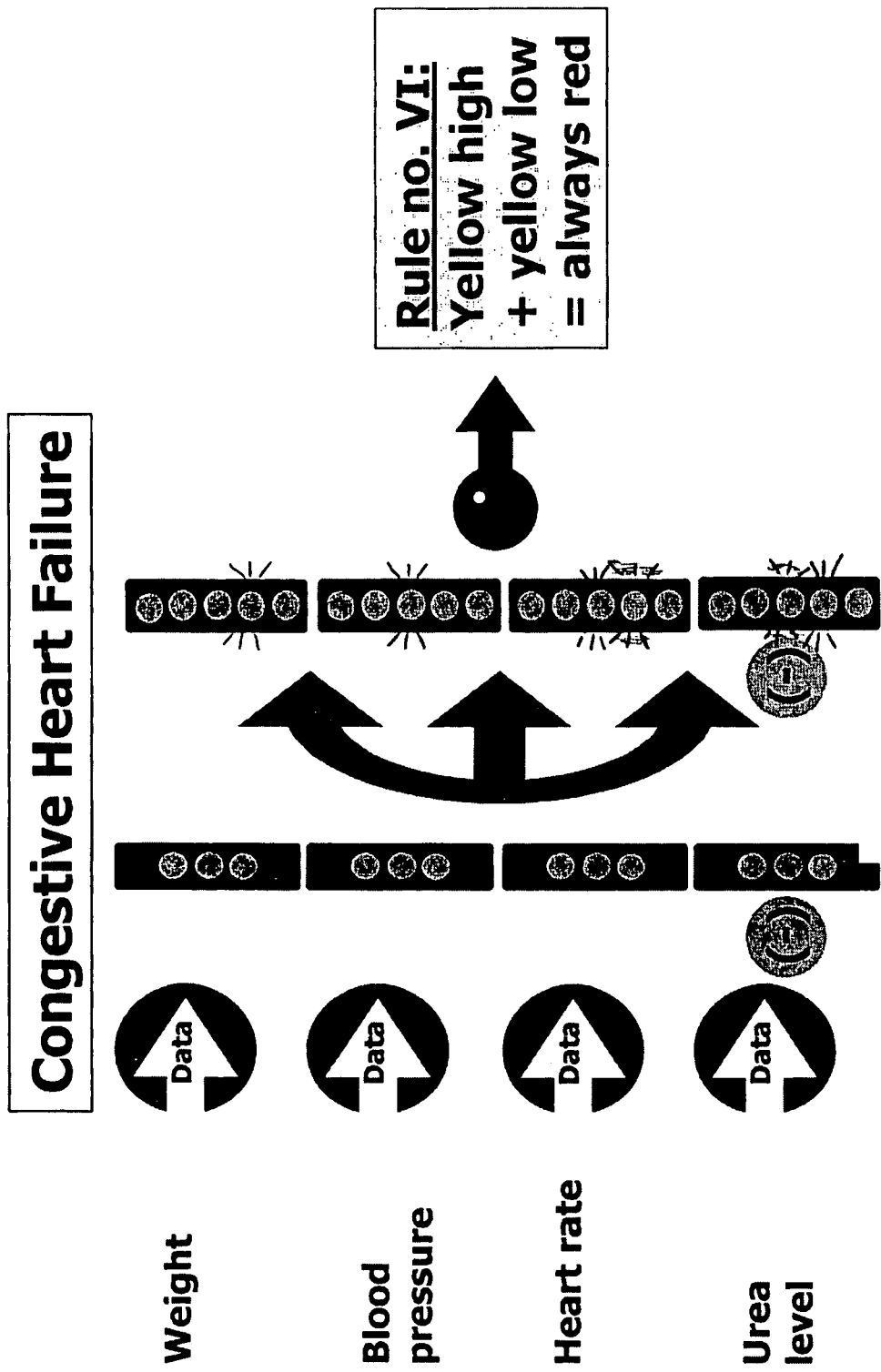

In FIG. 21b, weight is shown as a low amber result, blood pressure as a green result, heart rate as a low amber result, and urea level as a green result. The two amber results, being both low ambers, would not normally cause a red, however, because urea level is signed (i.e. polarized), it behaves as a high amber result, and triggers the rule that says that a high amber plus a low amber gives a consolidated result of red.

Figure 21C:
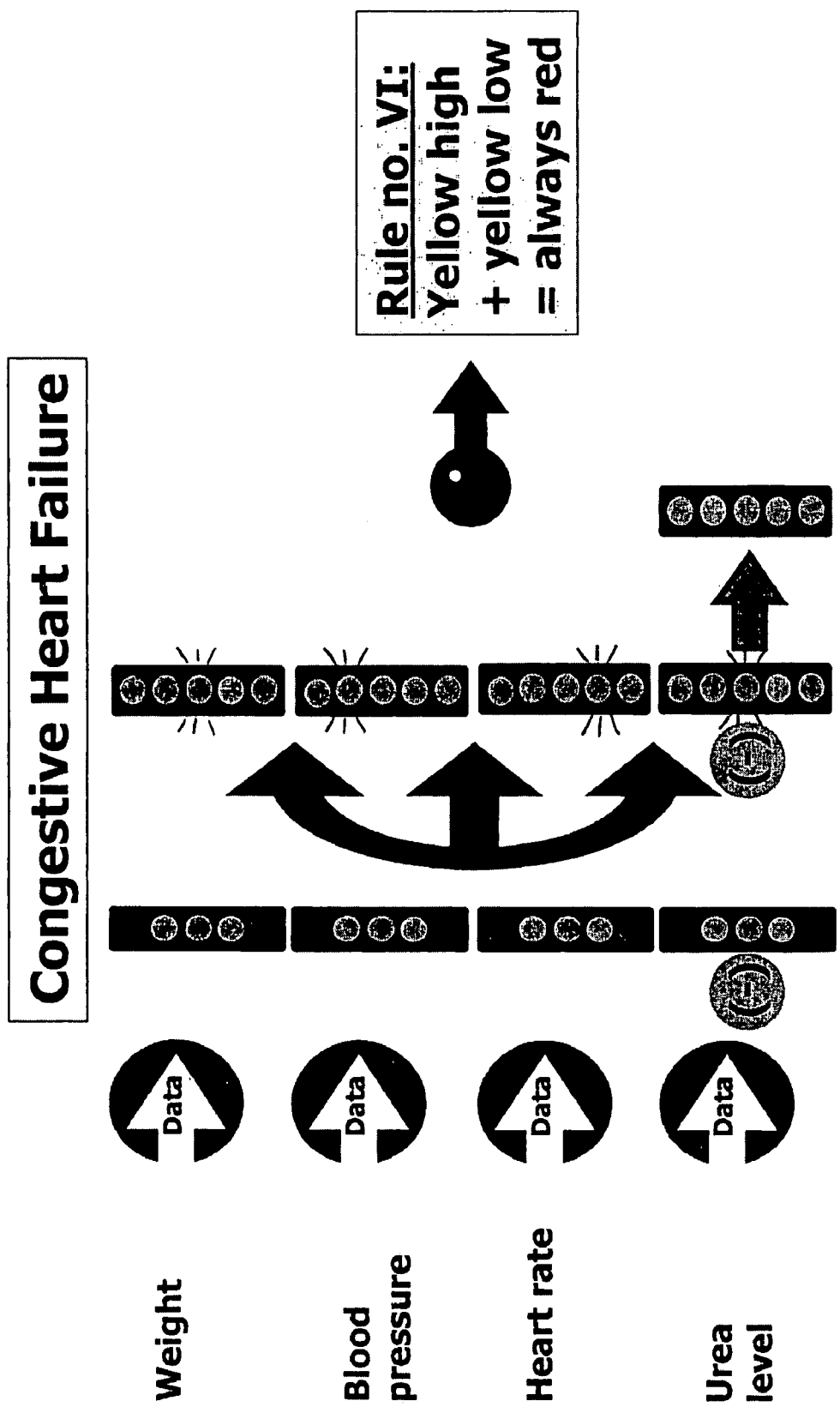

In FIG. 21c, weight is shown as a green result, blood pressure as a high amber result, heart rate as a low amber result, and urea level as a green result. The two amber results, one being a high amber and one being a low amber, trigger the rule that says that a high amber plus a low amber gives a consolidated result of red.

Figure 21D:
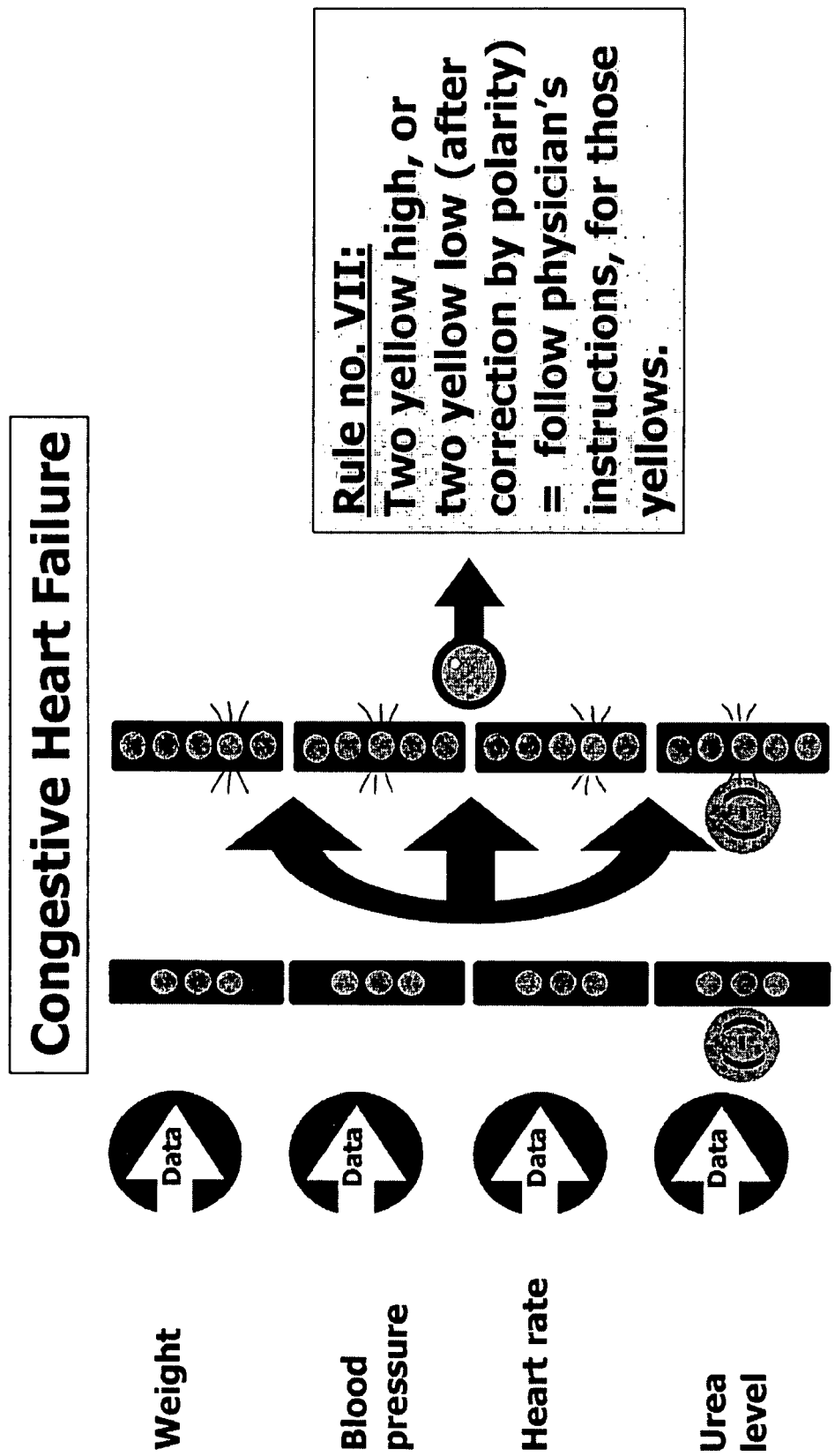

In FIG. 21d, weight is shown as a low amber result, blood pressure as a green result, heart rate as a low amber result, and urea level as a green result. The two amber results, both being low, do not trigger a red result, and the consolidated output is amber with recommendations for each of the individual ambers.

Figure 22:
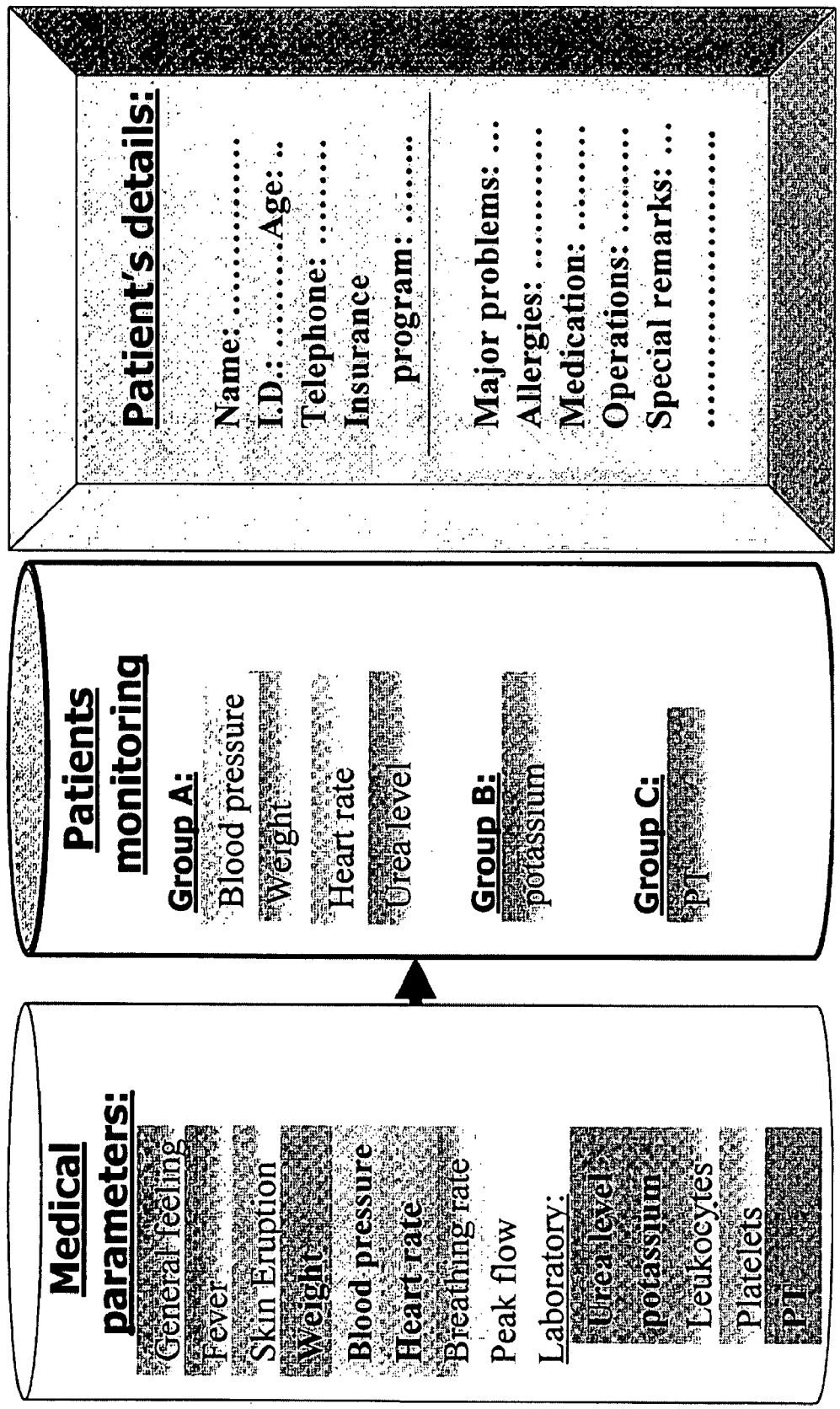
FIG. 22 is a generalized schematic diagram showing the data input form of FIG. 18 at a further stage in customization.

Reference is now made to FIG. 22 which is a generalized diagram showing an input form for programming a home monitoring system according to embodiments of the present invention. In FIG. 22, a full set of features that a physician may select for monitoring a patient suffering from congestive heart failure from a complete list of relevant parameters. Such selected parameters here include blood pressure, weight, heart rate, urea level, potassium level and PT.

In addition to studying congestive heart failure as described above, embodiments of the present invention are useful for monitoring patients suffering from any condition or illness or undergoing a course of treatment wherein continuous monitoring is needed. For example, it is also possible to monitor a patient for asthma. Relevant parameters for monitoring an asthma patient are heart rate, breathing rate and peak airflow.

A patient suffering from renal failure may also be monitored by the equipment of embodiments of the present invention. Typical parameters for selecting in the event of renal failure may be weight, urea level, potassium level and creatinine level.

The equipment of embodiments of the present invention may be used to monitor chemotherapy patients. A typical symptom that may be included in the case of a chemotherapy patient would be a burning sensation in the legs. Such a symptom is indicative to the physician that the treatment should be modified.

Figure 23:
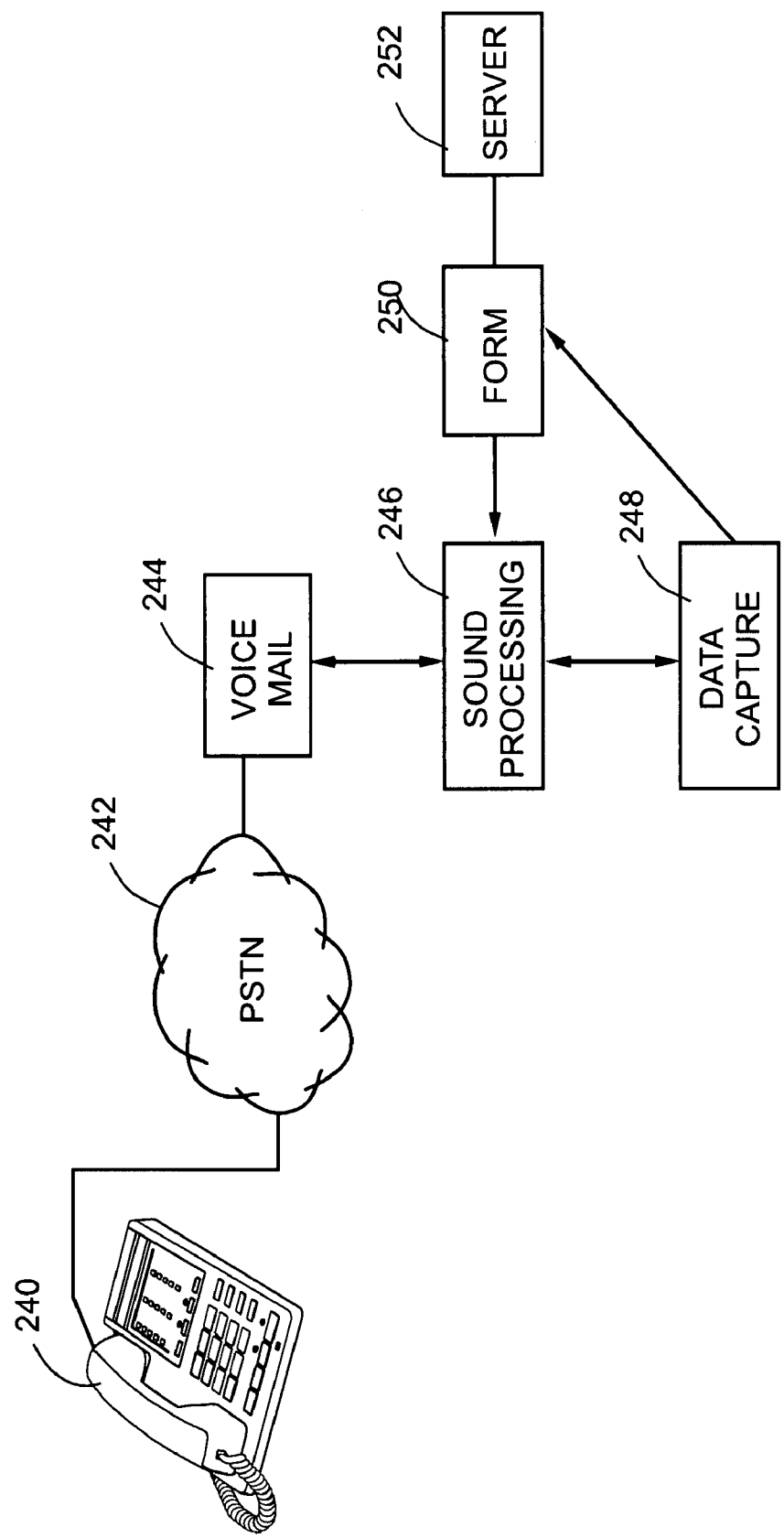
FIG. 23 is a generalized block diagram showing how a voice-mail system can be combined with data capture.

Reference is now made to FIG. 23, which is a simplified diagram of a system for data capture over a telephone line which may be used in embodiments of the present invention. In FIG. 23, a telephone 240 is connected via the public switched telephone network 242 to a voicemail box 244. The voicemail box 244 is connected to sound processing equipment 246 which is operable to recognize voice and tone input and convert it into textual form, and is able to output sound towards the telephone line, perhaps by using an electronic voice as a text to sound converter. A data capture unit 248 takes textual data from the sound processing unit 246 and places it on a form 250. The sound processing device is operable to take labels from the form and read them out over the telephone line to form the questions which the user is required to answer. When the form 250 is completed, following a question and answer session between the user and the system, the form is submitted to a server 252 for processing. An indication of his condition, and recommendations or instructions may then be read out automatically to the user.

In a variation of the embodiment of FIG. 23, in place of a textual form, data is entered in a format suitable for processing directly by the server.

Embodiments of the present invention thus provide a system in which parametric data is obtained from a patient and is processed according to a set of rules or filters which essentially quantize the data into primary categories.

The data that may be processed by the system includes primary data such as parametric data, and symptomatic data, and secondary data such as levels of change in the primary data.

Labels are associated with the categories and combinatorial rules allow for the selection of secondary categories. The secondary categories, which may occur at one or more levels, may also be associated with labels.

The filtering into primary and secondary categories may occur at the patient end, at a server or with a physician. The rules are preferably set on a per patient basis by the physician although the physician may use generalized templates from which to build an individual patient profile.

The physician is preferably able to obtain data about the patient in graphical format, conveniently showing trends and patterns. An upward trend in the data or a pattern showing large swings between high and low values may be a cause for concern even though the values themselves do not cross any preset or obvious danger thresholds.

The system allows the physician to modify the settings, on a per patient basis, in the light of his experience, research results or other information.

The system may utilize unified messaging for alerting the physician to dangerous or red states of the patient.

It will be appreciated that although the present invention has been illustrated in the context of medical decision-making it is applicable in all cases in which trustworthy decisions are needed without the continuous presence of a professional.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

The invention claimed is:

1. A parameter evaluation system, comprising:
 a boundary input device, user operable for setting internal boundaries at any of substantially continuous locations inside a variation range of one or more continuous parameters, said parameters being medical parameters and being individual to respective patients, said boundaries defining a plurality of internal regions within said variation range, said boundary input device thereby being able to allow user reconfiguration of said boundary regions, a label input device, user operable for associating labels with said internal regions, a rule input device, user operable for setting rules to associate at least one of a plurality of output recommendations with each of said internal regions and with combinations thereof, and an output device configured to present a user with an output recommendation associated with a respective said internal region or combination thereof, said output recommendation corresponding to at least one measured said medical parameter input to said system.

2. The system of claim 1, wherein said boundary input device comprises a bar having a length representative of a variation range of a respective parameter.

3. The system of claim 2, wherein said boundary input device further comprises slidable boundary points for sliding along said length and wherein said regions are defined between said slidable boundary points.

4. The system of claim 3 wherein said label input device is operable to associate one of a plurality of labeling colors with at least one of said regions.

5. The system of claim 3 wherein said label input device is operable to associate a labeling color with a combination of said regions.

6. The system of claim 1 in which said label input device is operable to label at least one of said regions with one of a group of categories.

7. The system of claim 6 in which at least one of said categories is associated with a procedure for making automatic contact with a remote site.

8. The system of claim 7 wherein said procedure utilizes any one of a group comprising internet messaging, telephone messaging, paging and fax messaging to reach said remote site.

9. The system of claim 1, further comprising an interface for connecting a measuring device thereto.

10. The system of claim 9 further comprising a measuring device attached to said interface for providing to said system a measured parameter.

11. The system of claim 1, wherein said parameter is a body medical parameter.

12. The system of claim 1, further comprising a list of at least one symptom, selectable by a user and classifiable by said user according to degree of severity, and wherein said rule input device is usable to set rules which incorporate said rule input device with said parameters to produce said output.

13. The system of claim 1 wherein at least one parameter is signable to influence an output.

14. The system of claim 1, wherein said measurement is inputtable to said system over a telephone via sound recognition apparatus able to interrogate a user and understand sound responses.

15. The system of claim 1, comprising a further output device, operable to output measurement data to show at least one of alarms, trends and data patterns.

16. The system of claim 1, further comprising a unified messaging hierarchy for communicating using a hierarchy of messaging modes.

17. The system of claim 1, wherein said boundary input device comprises:

a visual representation of said variation range as a linear continuum, a continuum divider for visually dividing said continuum at user selectable points therealong, said points corresponding to values of said parameter, thereby to define regions therebetween, a category definer for defining categories for association with said regions, and a category scorer for assigning a scoring value to each of said regions in accordance with a respective associated category, said scoring to comprise input to a predefined logical rule to arrive at a medical analysis that takes account of said parameter.

18. The system of claim 17, wherein said user selectable points are for selecting according to a patient medical history.

19. The system of claim 17, wherein said user selectable points are for changing dynamically with change in a patient's medical condition.

20. The system of claim 17, wherein said logical rule is a combining rule taking input from at least one other parameter.

21. A method of associating a series of outputs with detected levels of a continuously varying parameter, said detected levels comprising an outcome, the method comprising;

inviting a user to slidably set one or more internal boundary levels at any of substantially continuous locations inside a variation range of said parameter, said parameter being a medical parameter and being individual to respective patients, thereby defining internal regions between each boundary level, such that said internal regions are differentially definable for different patients, inviting a user to associate categorization labels with each said defined internal region, inviting a user to associate rules with each said internal region and with combinations of said internal regions of different said medical parameters to associate a series of outputs with said regions and combinations, such that at least one of said series of outputs is produced by an outcome.

22. A method according to claim 21, wherein at least one of said parameters is a body measurement and said output is a medical instruction.

* * * * *